United States Patent
Rylatt et al.

(10) Patent No.: US 8,951,749 B2
(45) Date of Patent: Feb. 10, 2015

(54) ENHANCED IMMUNOASSAY SENSOR

(75) Inventors: Dennis Rylatt, Wheelers Hill (AU); Alastair Hodges, Blackburn South (AU)

(73) Assignee: Universal Biosensors Pty Ltd, Rowville (AU)

( * ) Notice: Subject to any disclaimer, the term of this patent is extended or adjusted under 35 U.S.C. 154(b) by 128 days.

(21) Appl. No.: 13/003,752

(22) PCT Filed: Jul. 10, 2009

(86) PCT No.: PCT/IB2009/006688
§ 371 (c)(1), (2), (4) Date: Jan. 11, 2011

(87) PCT Pub. No.: WO2010/004436
PCT Pub. Date: Jan. 14, 2010

(65) Prior Publication Data
US 2011/0111425 A1    May 12, 2011

Related U.S. Application Data

(60) Provisional application No. 61/129,688, filed on Jul. 11, 2008.

(51) Int. Cl.
*G01N 33/53* (2006.01)
*G01N 33/543* (2006.01)
(Continued)

(52) U.S. Cl.
CPC .......... *G01N 33/54366* (2013.01); *G01N 33/53* (2013.01); *G01N 33/5302* (2013.01);
(Continued)

(58) Field of Classification Search
CPC .............. G01N 33/53; G01N 33/5302; G01N 33/5306; G01N 33/537; G01N 33/538; G01N 33/539; G01N 33/541; G01N 33/558; G01N 33/581; G01N 33/66; C12Q 1/001; C12Q 1/004; C12Q 1/005; C12Q 1/006; C12Q 1/26; C12Q 1/32

USPC ........... 435/7.7, 7.9, 4, 7.1, 14, 287.1, 287.2, 435/287.9, 288.3, 288.4, 288.5
See application file for complete search history.

(56) References Cited

U.S. PATENT DOCUMENTS

| | | | |
|---|---|---|---|
| 4,213,893 | A | 7/1980 | Carrico et al. |
| 4,622,294 | A | 11/1986 | Kung et al. |

(Continued)

FOREIGN PATENT DOCUMENTS

| | | |
|---|---|---|
| EP | 0 300 628 | 1/1989 |
| EP | 1 347 302 | 9/2003 |

(Continued)

OTHER PUBLICATIONS

Decory, et al. "Development of an Immunomagnetic Bead-Immunoliposome Fluorescence Assay for Rapid Detection of *Escherichia coli* 0157:H7 in Aqueous Samples and Comparison of the Assay with a Standard Microbiological Method," Appl. Environ Microbial., 2005, pp. 1856-1864, 71.

(Continued)

*Primary Examiner* — Melanie Y Brown
*Assistant Examiner* — Erik B Crawford
(74) *Attorney, Agent, or Firm* — Davis Wright Tremaine LLP

(57) ABSTRACT

Disclosed herein are devices for detecting the presence of a target analyte in a fluid sample. The biosensor device can comprise at least a reaction chamber and a detection chamber. The device can comprise a amplifying mechanism such that one target analyte molecule present in the fluid sample can lead to generation/activation of multiple detection agent molecules, and therefore, an amplified signal. Also disclosed are the methods of manufacturing and using such a biosensor device.

23 Claims, 7 Drawing Sheets

(51) Int. Cl.

| | |
|---|---|
| *G01N 33/537* | (2006.01) |
| *G01N 33/538* | (2006.01) |
| *G01N 33/539* | (2006.01) |
| *G01N 33/541* | (2006.01) |
| *G01N 33/558* | (2006.01) |
| *G01N 33/58* | (2006.01) |
| *G01N 33/66* | (2006.01) |
| *C12Q 1/00* | (2006.01) |
| *C12Q 1/26* | (2006.01) |
| *C12Q 1/32* | (2006.01) |
| *B01L 3/00* | (2006.01) |

(52) U.S. Cl.
CPC .......... *G01N33/5306* (2013.01); *G01N 33/537* (2013.01); *G01N 33/538* (2013.01); *G01N 33/539* (2013.01); *G01N 33/541* (2013.01); *G01N 33/558* (2013.01); *G01N 33/581* (2013.01); *G01N 33/66* (2013.01); *C12Q 1/001* (2013.01); *C12Q 1/004* (2013.01); *C12Q 1/005* (2013.01); *C12Q 1/006* (2013.01); *C12Q 1/26* (2013.01); *C12Q 1/32* (2013.01); *B01L 3/5027* (2013.01); *G01N 33/54393* (2013.01); *B01L 2200/0621* (2013.01); *B01L 2200/10* (2013.01); *B01L 2300/0645* (2013.01); *B01L 2300/0825* (2013.01); *B01L 2300/087* (2013.01); *B01L 2400/0406* (2013.01); *B01L 2400/0694* (2013.01)
USPC .................. 435/7.7; 435/4; 435/7.1; 435/14; 435/287.1; 435/287.2; 435/287.9; 435/288.3; 435/288.4; 435/288.5

(56) References Cited

U.S. PATENT DOCUMENTS

| | | | |
|---|---|---|---|
| 5,156,972 | A | 10/1992 | Issachar |
| 5,965,456 | A | 10/1999 | Malmqvist et al. |
| 6,083,708 | A | 7/2000 | Singh et al. |
| 2003/0180814 | A1 | 9/2003 | Hodges et al. |
| 2004/0050717 | A1* | 3/2004 | Teodorczyk et al. ...... 205/777.5 |
| 2004/0203137 | A1 | 10/2004 | Hodges et al. |
| 2006/0134713 | A1 | 6/2006 | Rylatt et al. |
| 2006/0226008 | A1 | 10/2006 | Rodgers et al. |
| 2007/0131549 | A1 | 6/2007 | Cai et al. |
| 2007/0289880 | A1 | 12/2007 | Zweig |

FOREIGN PATENT DOCUMENTS

| | | |
|---|---|---|
| JP | 7227298 | 8/1995 |
| WO | WO 86/00142 | 1/1986 |
| WO | WO 92/03730 | 3/1992 |
| WO | WO 96/24062 | 8/1996 |
| WO | WO 97/07398 | 2/1997 |
| WO | WO 97/27474 | 7/1997 |
| WO | WO 98/04743 | 2/1998 |
| WO | WO 98/20332 | 5/1998 |
| WO | WO 99/10743 | 3/1999 |
| WO | WO 99/18433 | 4/1999 |
| WO | WO 00/62351 | 10/2000 |
| WO | WO 02/07635 | 1/2002 |
| WO | WO 02/08763 | 1/2002 |
| WO | WO 02/12885 | 2/2002 |
| WO | WO 02/40058 | 5/2002 |
| WO | WO 02/082078 | 10/2002 |
| WO | WO 03/097863 | 11/2003 |
| WO | WO 03/101427 | 12/2003 |
| WO | WO 2004/041774 | 5/2004 |
| WO | WO 2004/046717 | 6/2004 |
| WO | WO 2005/000902 | 1/2005 |
| WO | WO 2005/116654 | 12/2005 |
| WO | WO 2006/035431 | 4/2006 |
| WO | WO 2006/046524 | 5/2006 |
| WO | WO 2006/096619 | 9/2006 |
| WO | WO 2006/127167 | 11/2006 |
| WO | WO 2007/025558 | 3/2007 |

OTHER PUBLICATIONS

Intellectual Property Office of New Zealand, Examination Report in corresponding New Zealand application No. 590411, issued on Jan. 26, 2012, 2 pages.
PCT, International Search Report and Written Opinion issued in corresponding international application No. IB2009/006688, mailed on Dec. 23, 2009, 15 pages.
U.S. Appl. No. 61/129,688.
Heiss, et al., "Dip-and Read Test Strips for the Determination of Trinitroltoluene (TNT) in Drinking Water," Analytica Chimica ACTA, 396(2/03):309-16 (1999).
European Patent Office, Extended European Search Report in corresponding European Application No. 09794067.0, mailed on Aug. 19, 2011, 10 pages.
Notice of Rejection, mailed in related Japanese Patent Application No. 2011-517271, dated Oct. 29, 2013, 2 pages.
Israel Patent Office Ministry of Justice, "Official Action (English translation only)," in counterpart Israeli Patent Application No. 210543, dated Apr. 3, 2014, 1 pg.

* cited by examiner

ENHANCED IMMUNOASSAY SENSOR

CROSS-REFERENCE TO RELATED APPLICATIONS

The present application is a U.S. National Stage entry under 35 U.S.C. §371 of International Application No. PCT/IB2009/006688, filed on Jul. 10, 2009, designating the United States of America and published in English on Jan. 14, 2010, which in turn claims priority to U.S. Provisional Application No. 61/129,688, filed on Jul. 11, 2008, each of which is hereby incorporated by reference in its entirety.

RELATED APPLICATIONS AND INCORPORATIONS BY REFERENCE

This application claims priority of U.S. Provisional Application Ser. No. 61/129,688 (entitled "Enhanced Immunoassay Sensor", filed on Jul. 11, 2008). This application claims priority as a continuation-in-part to U.S. application Ser. No. 11/284,097 (entitled "BIOSENSOR APPARATUS AND METHODS OF USE," filed Nov. 21, 2005), which in turn claims priority as a continuation-in-part to U.S. application Ser. No. 10/105,050 ("DIRECT IMMUNOSENSOR ASSAY," filed Mar. 21, 2002) and Ser. No. 10/830,841 (entitled "IMMUNOSENSOR," filed Apr. 22, 2004). All of the foregoing applications are incorporated herein by reference in their respective entireties.

U.S. application Ser. No. 11/284,097 was published as Pub. No. US 2006/0134713 on Jun. 22, 2006. U.S. application Ser. No. 10/105,050 was published as Pub. No. US 2003/0180814 on Sep. 25, 2003. U.S. application Ser. No. 10/830,841 was published as Pub. No. US 2004/0203137 on Oct. 14, 2004.

The following references are respectively incorporated by reference in their entireties: (1) EPO 0300628; (2) JP 7227298; (3) U.S. Pat. No. 4,622,294; (4) US 2006226008; (5) US 2007131549; (6) WO02012885; (7) WO0240058A2; (8) WO0207635; (9) WO02082078; (10) WO 02082078; (11) WO 03097863; (12) WO 03101427; (13) WO04041774; (14) WO 05000902; (15) WO05116654; (16) WO 06035431; (17) WO1992003730; (18) WO2000062351; (19) WO2004046717; (20) WO 2006046524; (21) WO 2006096619; (22) WO 2006127167; (23) WO 9203730; (24) WO 9203730A1; (25) WO 9820332; (26) WO 96024062; (27) WO 98004743; (28) WO 99010743; and (29) Thomas R. DeCory, Richard A. Durst, Scott J. Zimmerman, Linda A. Garringer, Gary Paluca, Heleen H. DeCory, and Richard A. Montagna. "Development of an Immunomagnetic Bead-Immunoliposome Fluorescence Assay for Rapid Detection of *Escherichia coli* O157:H7 in Aqueous Samples and Comparison of the Assay with a Standard Microbiological Method." *Appl. Environ Microbial.* 2005, 71:1856-1864. All of the foregoing references are incorporated herein by reference in their respective entireties.

BACKGROUND

Conventional biomedical sensors, including immunoassays based systems, have been used to report the presence and/or concentration of a wide variety of analytes. Immunoassays are generally classified into two categories: competition assays and sandwich assays. In a competition assay, the antigen in the test sample is mixed with an antigen-probe complex (commonly referred to as a reporter complex) and the mixture then competes for binding to the antibody. In a sandwich immunoassay, the antigen in the test sample binds to the antibody and then a second antibody-probe complex binds to the antigen. In these prior art assay methods, one or more washing steps are usually required. The washing steps can introduce complexity into the assay procedure and can generate biohazardous liquid waste.

Immunoassays usually provide a user with either a qualitative result (e.g., a "yes/no answer") obtained, most often by a simple visual detection (e.g., color change), or a quantitative result such as a concentration of an antigen. Most of the quantitative methods involve expensive pieces of equipment, such as scintillation counters (for monitoring radioactivity), spectrophotometers, spectrofluorimeters (see, e.g., U.S. Pat. No. 5,156,972), surface plasmon resonance instruments (see, e.g., U.S. Pat. No. 5,965,456), and the like. It would therefore be advantageous to develop an immunoassay that is both inexpensive and simple enough to use to be suitable for home or field use. Such an biosensor would preferably require no centrifugation, dilution, pipetting, washing, or timing steps, and would generate minimal waste.

SUMMARY

Some embodiments of the disclosure comprise a device for detecting a target analyte in a fluid sample, the device comprising: a reaction chamber, wherein the reaction chamber comprises internal surfaces, a binding agent and a probe agent, the probe agent comprising a binding partner and a vehicle, wherein the binding partner is bound to the vehicle, wherein the target analyte in the fluid sample can react with the binding agent or the binding partner; a detection chamber; and a fluid passageway between the reaction chamber and the detection chamber, wherein the device is adapted to move the reacted fluid sample from the reaction chamber to the detection chamber through the fluid passageway via capillary action, and wherein the presence of the target analyte in the fluid sample at a concentration results in a change in the amount of probe agent that moves with the reacted fluid sample to the detection chamber, wherein the change is detectable in the detection chamber and dependent on at least a threshold of the concentration. The device can further comprise a fill chamber, wherein the fill chamber comprises internal surfaces. The internal surfaces of the reaction chamber and the fill chamber can comprise internal walls, and/or the surfaces of at least one supporting material. The reaction chamber can comprise an opening to the atmosphere.

The reaction chamber and/or the fill chamber can comprise a blocking agent, wherein the blocking agent is capable of preventing non-specific binding of proteins or lipidic particles to the internal surfaces of the reaction chamber. A lipidic particle can comprise liposomes, vesicles, cellular organelles, and the like. The blocking agent can comprise at least one selected from a surfactant and a blocking protein. The blocking protein can comprise bovine serum albumin.

The binding agent molecules and the probe agent molecules can be bound to different internal surfaces of the reaction chamber.

The binding agent can comprise at least one magnetic bead. The device can comprise a magnetic field to serve to confine the binding agent coated on magnetic beads in the reaction chamber.

The vehicle of a probe agent molecule can comprise at least one copy of an activating agent. The vehicle can comprise from about 10 to about 100000 copies of an activating agent. The activating agent can be encapsulated within a vehicle which can comprise at least one lipidic particle. A lipidic particle can comprise liposomes, vesicles, cellular organelles, and the like. The activating agent can be surface bound to a vehicle which can comprise at least one polymer. The polymer can comprise a dendrimer.

The binding partner of the probe agent can be adapted to bind to the binding agent, or the target analyte which is bound to the binding agent, or the target analyte which is not bound to the binding agent.

The reaction chamber can comprise an unactivated agent immobilized in the reaction chamber, wherein the unactivated agent can bind to an unbound or unencapsulated activating agent. The unactivated agent can comprise at least one magnetic bead, and can be confined within the reaction chamber by a magnetic field.

The fill chamber and/or the reaction chamber can comprise a buffer which can adjust the pH of a fluid sample. The buffer can comprise a substance selected from phosphate, citrate, citraconate, mellitate, tris, pipes, mops, hepes, phthalate, imadazole.

The detection chamber can comprise a liberating agent, wherein the liberating agent can liberate the activating agent from the vehicle. The liberating agent can comprise at least one agent selected from a mild detergent, a lytic peptide, an enzyme, heating, cooling, ultrasonication and a light source together with a photochemically activated lysing agent which is incorporated into the vehicle. The mild detergent can comprise one detergent selected from n-octyl-B-D-glucopyranoside, TWEEN® 20 (Polysorbate 20), BRIJ® 35 (polyethylene glycol lauryl ether) and TRITON™ X-100 (a polyoxyethylene octyl phenyl ether). The lytic peptide can comprise one peptide selected from mellitin, and one of a class of phospholipases, a component of the complement system. The enzyme comprises one enzyme selected from a protease and trypsin. The liberating agent can comprise a physical means, such as, for example, cooling, heating, ultrasonication, or a combination of physical and chemical means, such as, for example, a photochemical reaction initiated by a light source directed into the sensor.

The activating agent can comprise a cofactor for an enzyme. The detection chamber can comprise an apo-enzyme which can be activated by the cofactor. The enzyme can comprise glucose oxidase. The cofactor/apo-enzyme pair can comprise flavin adenine dinucleotide and apo-glucose oxidase. The enzyme can comprise a glucose dehydrogenase. The cofactor/apo-enzyme pair can comprise pyrolloquinoline quinone (PQQ) and apo-glucose dehydrogenase (GDH). The detection chamber can further comprise an enzyme substrate. The enzyme substrate can comprise an oxidizable substrate. The oxidizable substrate can comprise one substrate selected from galactose, maltose, xylose, and acetic acid. The enzyme substrate can comprise glucose. The detection chamber can further comprise at least one mediator. The mediator can comprise at least one substance selected from dichlorophenolindophenol, phenazine ethosulphate, ferricyanide, ferrocene and complexes between transition metals and nitrogen-containing heteroatomic species.

The detection chamber can comprise a vent at the distal end. The vent can be opened by piercing an outer layer of the device, or by removing a portion of an outer layer of the device.

The detection chamber can comprise at least two electrodes for detecting an electrochemical reaction in the detection chamber. At least one of the electrodes can be formed from an electrically conductive layer. The detection chamber can comprise a break in the electrically conductive layer that can serve to define at least one edge of the electrode in the detection chamber. At least one electrode can comprise palladium, platinum, gold, iridium, carbon, carbon mixed with binder, indium oxide, tin oxide or a mixture thereof. A change in the amount of the probe agent in the detection chamber can be detected via an electrochemical reaction in the detection chamber.

Some embodiments of the disclose comprise a method of detecting a target analyte in a fluid sample, comprising: delivering the fluid sample to a device, wherein the device comprises a reaction chamber and a detection chamber, the reaction chamber comprising a binding agent and a probe agent, the probe agent comprising a binding partner and a vehicle; allowing a reaction to proceed in the reaction chamber between the binding agent and the probe agent, wherein the presence of the target analyte in the fluid sample at a concentration results in changes in the amount of probe agent bound in the reaction chamber and in the amount of unbound probe agent, wherein the changes are dependent on the concentration of the target analyte; moving the reacted sample fluid from the reaction chamber into the detection chamber by capillary action such that the unbound probe agent moves to the detection chamber; and detecting presence of the probe agent in the detection chamber via a detecting agent. The sample can be delivered to the device through a fill chamber of the device via a capillary action. The detecting agent can comprise an apo-enzyme. The vehicle can comprise at least one copy of an activating agent, wherein one copy of the activating agent can activate at least one copy of the detecting agent. Moving the sample from the reaction chamber to the detection chamber can comprise opening a vent. The detecting can comprise quantifying electrical signals received from the detection chamber, wherein the magnitude of the electrical signals can be dependent on the concentration of the target analyte in the sample fluid.

DETAILED DESCRIPTION

Figure 1A:
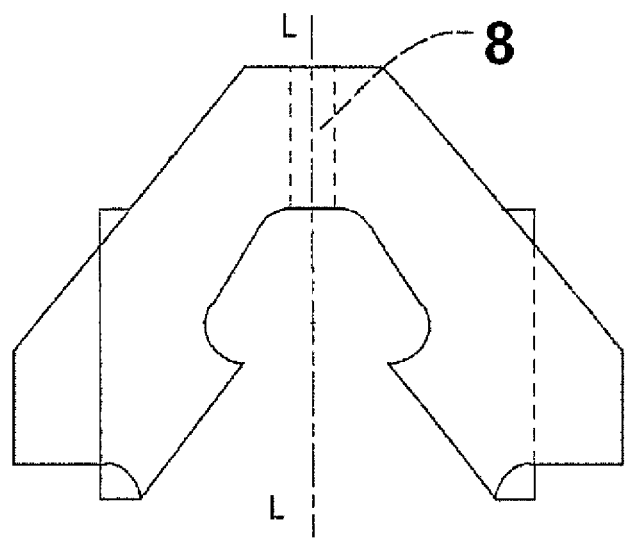
FIG. 1A illustrates an exemplary U-shape biosensor. Part 8 is where the reaction and detection can occur.

Various exemplary embodiments are discussed in detail below including a preferred embodiment. While specific implementations are discussed, it should be understood that this is done for illustration purposes only. A person skilled in the relevant art can recognize that the systems, methods and features provided herein can be used without parting from the spirit and scope of the invention. Furthermore, any and all references cited herein shall be incorporated herein by reference.

Glucose dehydrogenase (GDH) is a pyrolloquinoline quinone (PQQ), which can comprise bacterial enzyme, commercially available in recombinant form both with and without its PQQ cofactor.

In an exemplary embodiment, a biosensor can comprise an electrochemical cell using a potentiostat capable of measuring changes of 1 microampere per minute, it can be estimated that 1 ug/ml of GDH added to whole blood can be electrochemically detected using a glucose solution containing Potassium Ferricyanide previously dried down in the chamber. Potassium ferricyanide can act as the mediator for transport of electrons from the substrate to the electrode. If, in addition, a second mediator, such as Phenazine Ethosulphate (PES), which can make this transfer process more efficient, can also dried down into the chamber of the biosensor, as little as 50 ng/ml GDH can he reliably detected using the same potentiostat.

In an exemplary embodiment, if GDH can be coupled to antibody in a way that maintains both binding activity of the antibody and the GDH activity, then using the electrochemical detection system described above, 50 ng/ml for an antigen the same size as GDH, or 500 pM in molar terms, can be detected. For many antigens, for example, C reactive protein and D dimer, this can be sufficient to allow the measurement of the full range of concentrations found in an exemplary patient population.

However, there can be many antigens for which the useful clinical range can be lower than the foregoing. These include, for example, many cytokines, hormones such as Thyroid Stimulating hormone (TSH) and the myocardial infarction markers such as Troponin I and Pro BNP. In exemplary embodiments, these can be present at much lower concentrations, for example, 1-10 pM or sub pM ranges.

In an exemplary embodiment, a method can be provided which can allow rapid detection of antigens at these lower levels. The method can use a format similar to U.S. application Ser. No. 11/284,097, but can combine this with the two addition properties of the bacterial GDH enzyme. In exemplary embodiments, firstly there can be a requirement for activity for the cofactor PQQ, and secondly the inactive apoenzyme and PQQ can recombine under normal pH conditions to form stable active enzyme.

Mechanism

As stated above, the present embodiments can be applicable to a disposal or non-disposable biomedical strip or sensing device which can be used to report the presence and/or concentration of a wide variety of analytes via, such as, for example, binding reactions. As used herein, a binding reaction can refer to any reaction which involves at least two species binding together. It can comprise a competitive binding assay, a displacement binding assay, a double-antibody sandwich assay, or the like.

Merely for the purpose of convenience, the mechanism of how such a biosensor can work is described in terms of a biosensor with two chambers, a reaction chamber and a detection chamber, which can be used to test the presence and/or concentration of a target antigen in a fluid sample. It is understood that this is done for illustration purpose only, and is not intended to limit the scope of the disclosure.

The reaction chamber of the biosensor can comprise antibodies to the target antigen. The antibodies can be immobilized within the reaction chamber. The reaction chamber can comprise probe agent molecules which can bind to the immobilized antibodies and/or the target antigen. The probe agent molecules which are not bound to the immobilized antibodies due to the presence of the target antigen in the fluid sample can move to the detection chamber with the fluid sample. Each of the probe agent molecules can comprise multiple copies of an activating agent. The detection chamber can comprise detecting agent molecules which can be activated by the activating agent. The activated detecting agent can generate a signal which can be measured in the detection chamber, and the results can indicate, qualitatively and/or quantitatively, the presence and/or concentration of the target antigen in the fluid sample. The reaction chamber and detection chamber can be arranged such that the fluid sample can flow from the reaction chamber into the detection chamber in a controlled manner.

A fluid sample can enter the reaction chamber, wherein components of the fluid sample can undergo an immunological reaction. For example, one target antigen can bind to one immobilized antibody and/or one probe agent molecule. After the immunological reaction has taken place in the reaction chamber, at least some of the probe agent molecules can be transferred with the reacted fluid sample to the detection chamber. The number of the probe agent molecules flowing into the detection chamber can be dependent on the presence and/or concentration of the target antigen in the fluid sample. One probe agent molecule can comprise multiple copies of an activating agent. If one activating agent molecule can activate one detecting agent molecule and generate a unit of signal, then one probe agent molecule flowing into the detection chamber can generate multiple units of signal. This can increase the sensitivity, and/or accuracy, and/or rate, of the test. The signal can be measured and processed to generate a result indicating the presence and/or concentration of the target antigen.

In an exemplary embodiment, the binding reaction can be between any two species that bind to one another. The probe agent can be any agent that can lead to the generation of a detectable signal in the detection chamber.

To facilitate an understanding of certain exemplary embodiments, an example can be used of the binding agent comprising an antibody, the target analyte comprising an antigen which can bind to the binding agent, and the probe agent comprising an antigen which can bind to the binding agent, but with lower binding affinity compared to the target analyte. The antibody can be immobilized by coated onto a magnetic bead which is confined in the reaction chamber by a magnetic field. The probe agent can comprise an encapsulated enzyme cofactor for pyrolloquinoline quinone (PQQ) glucose dehydrogenase (GDH). The cofactor can combine with the apo GDH enzyme in the detection chamber, which can lead to the production of an electrical signal. If an encapsulated particle comprises, for example, 100 or more PQQ molecules, each of these can bind to and activate one apo-GDH molecule, then the inhibition of a single antibody-PQQ-liposome binding to the magnetic beads can lead to the activation of 100 or more GDH molecules. In this way, as little as 5 pM antigen, for example, can be detected, if for example each liposome contains 100 PQQ's, or 500 fM if each contains 1000 PQQ's.

However it is to be explicitly understood that (1) the binding agent, and/or the target analyte, and/or the probe agent can be, for example, any species that can bind to one another, (2) the probe agent can be, for example, any agent which can lead to a detectable signal in the detection chamber, wherein the probe agent can activate multiple signal generation agent molecules in the detection chamber, and (3) the signal detection method can be any suitable method, such as electrochemical and/or optical absorption and/or fluorescence.

Biosensor

The device can comprise one chamber, wherein the reaction and the detection can occur in the same chamber. The device can comprise two chambers, a reaction chamber and a detection chamber. The device can comprise more than two chambers. Merely by way of example, the device can comprise a fill chamber, in addition to the reaction chamber and the detection chamber. The device can comprise one reaction chamber and two detection chambers, such that more than one signal can be detected based on the same or different detection mechanisms in one test. The signals can be processed by way of, such as, for example, averaging, to improve the accuracy of the result. The signals indicating different parameters can be detected in one test. Merely by way of example, different inflammation cytokines related to cardiovascular diseases can be measured at the same time in one test, which can provide more accurate prediction and/or monitoring of the status of the disease. If the device have two or more chambers, any pair of these chambers can be in direct fluid communication with each other. As used herein, "direct" indicates that the pair of chambers can be in series connection and/or can exchange fluid directly, not through a third chamber. Some chambers can be in parallel connection and/or can exchange fluid through a third chamber. There can be a fluid passageway between a pair of chambers through which the fluid sample can flow from one chamber to the other. The flow through the fluid passageway can be controlled by a force balance via, such as, for example, a capillary action, a pneumatic pressure, an external force, or the like, or any combination thereof.

Figure 1B:
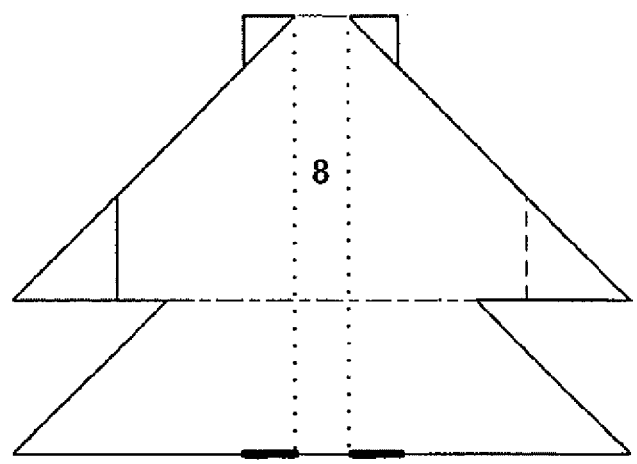
FIG. 1B illustrates an exemplary tree-shape biosensor. Part 8 is where the reaction and detection can occur.

The biosensor can have a shape, such as, for example, a generally "V" shape, as illustrated in FIG. 1A, a "tree" configuration as illustrated in FIG. 1B, a rectangular configuration illustrated in FIGS. 2-7, or the like. In FIGS. 1A and B, part 8 can be where the reaction chamber and/or detection chamber locate.

Figure 2:
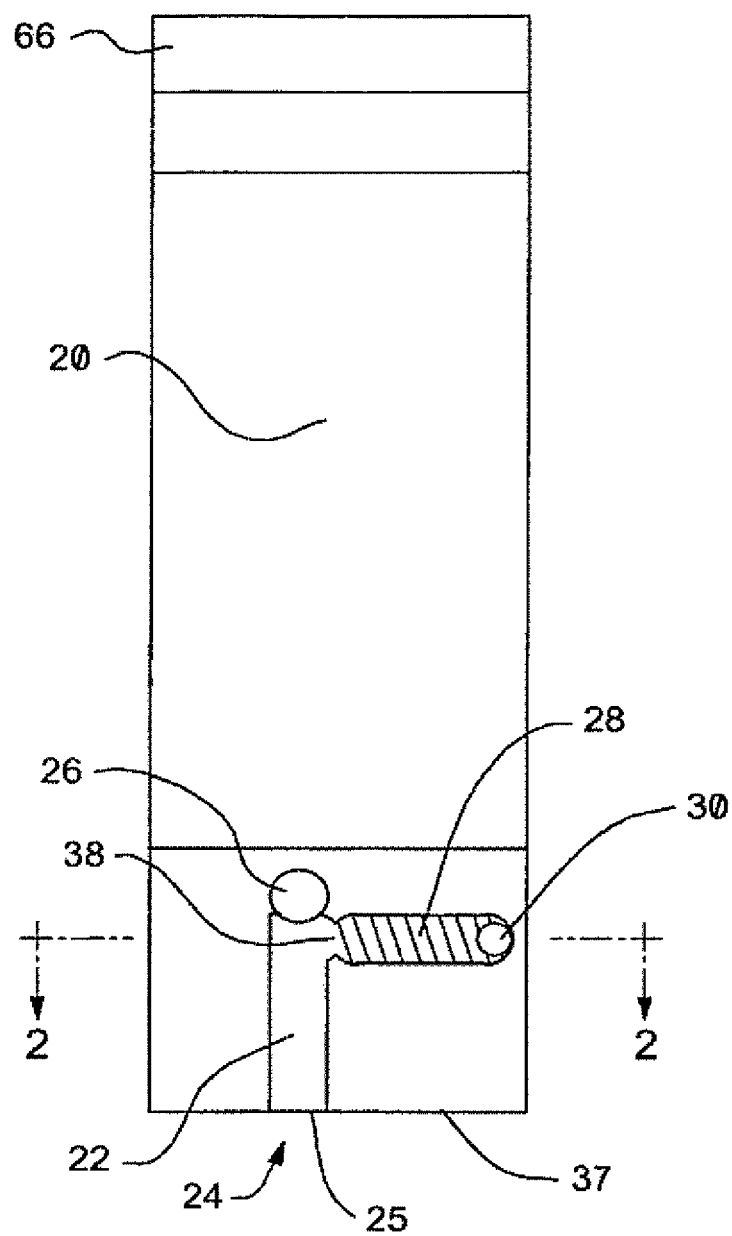
FIG. 2 is a top view of one embodiment of an biosensor disclosed herein.

FIG. 2 is an exemplary illustration of a biosensor. Sensor 20 can comprise a reaction chamber 22, a detection chamber 28, a sample passageway 38 between the chambers 22 and 28. Vent 30 can locate at the distal end of the detection chamber 28. Reaction chamber 22 can comprise an ingress 25 at the proximal end 24 of reaction chamber 22 at edge 37 of sensor 20. Contact area 66 can locate at an end of Sensor 20, and can electrically connect the sensor with a meter (not shown). Reaction chamber 22 can comprise a vent 26 that can be open to the atmosphere, thus allowing air displaced by a fluid sample to escape. A fluid sample can be drawn into reaction chamber 22 until it is filled up to the reaction chamber vent 26, whereupon filling can stop. The volume of reaction chamber 22 is chosen so as to be at least equal to and preferably larger than the volume of detection chamber 28.

Figure 3:
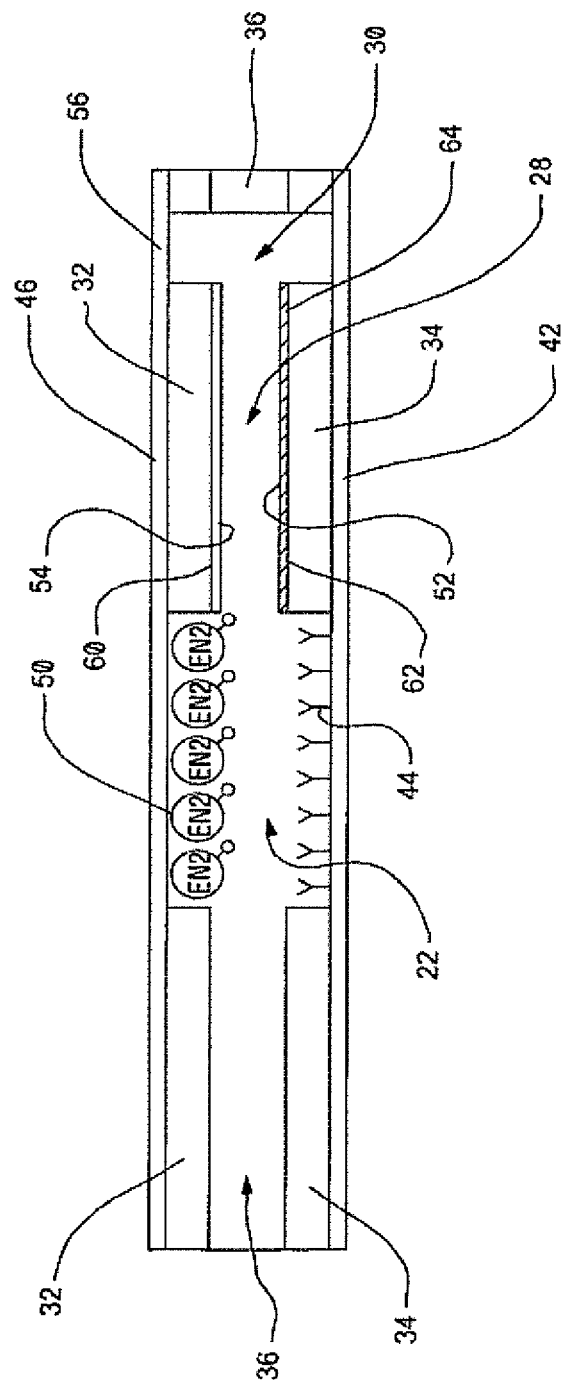
FIG. 3 is a cross-sectional view of the biosensor of FIG. 2 along line 2-2.

FIG. 3 is a cross-sectional view of the biosensor of FIG. 2 along line 2-2. The middle sheet 36 of sensor 20 has an aperture defining the sidewalls of reaction chamber 22 and detection chamber 28. Middle sheet 36 is sandwiched between one or more additional layers 32, 34, the additional layers 32 and 34 having an aperture corresponding only to reaction chamber 22. With respect to detection chamber 28, layers 32 and 34 can define the end walls 60, 62 (i.e., top and bottom surfaces) of the chamber. The end walls 60 and 62 of the detection chamber comprise electrodes 54 and 52, electrically connectable, via connection means, to a measuring circuit. Reaction chamber 22 can comprise immobilized binding agent molecules 44 on one internal surface, and probe agent molecules 50 on an opposing internal surface. Detection chamber 28 can comprise electrodes 54 and 52, reagents coated on at least one internal surface, such as, enzyme substrate 64, and vent 30 at the distal end of the chamber. The outer layers 42 and 46 extend longitudinal through sensor 20, and are not pierced initially. A portion of layer 46 can be removed at 56 to open the vent 30. Vent 56 can be opened in a variety of ways, including, for example, by puncturing an outer layer of the device, by removing a portion of the outer layer of the device, and/or by tearing away a portion of the device.

Figure 4:
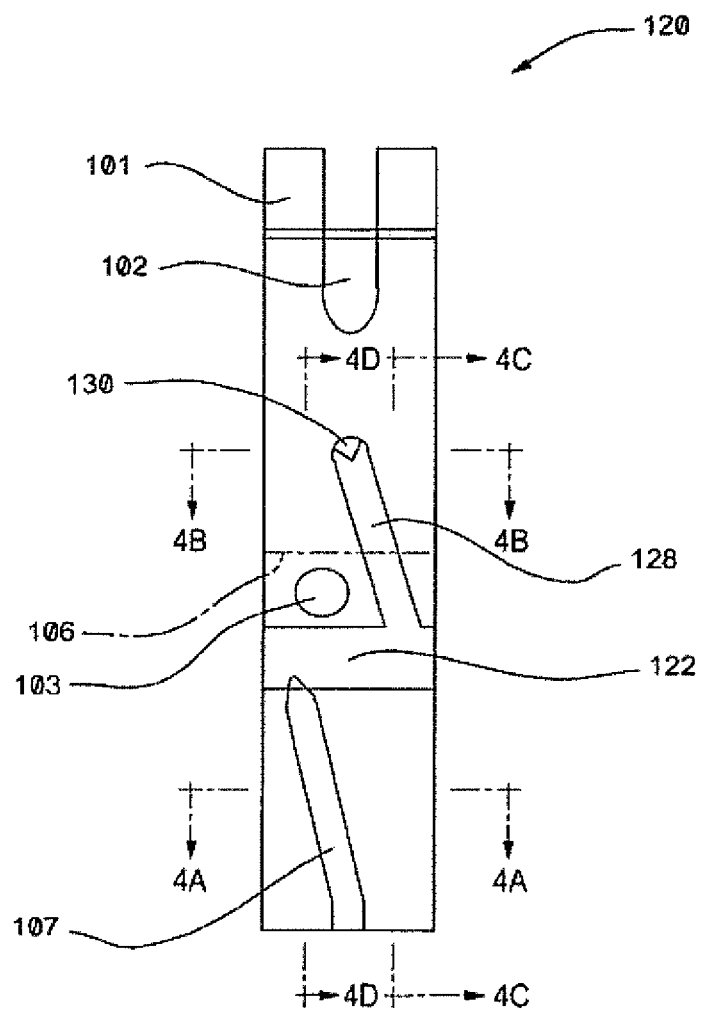
FIG. 4 is a top view of another embodiment of a biosensor disclosed herein.

FIG. 4 is a top view of another embodiment of biosensor 120. Sensor 120 can comprise fill chamber 107, reaction chamber 122, and detection chamber 128. The three chambers are in serial connection in terms of the fluid communication. Scratch 106 can locate near the proximal end of detection chamber 128. Vent 130 can locate at the distal end of detection chamber 128. Electrical contact areas 101, 102 and 103 can electrically connect the sensor to a meter.

Figure 5A:
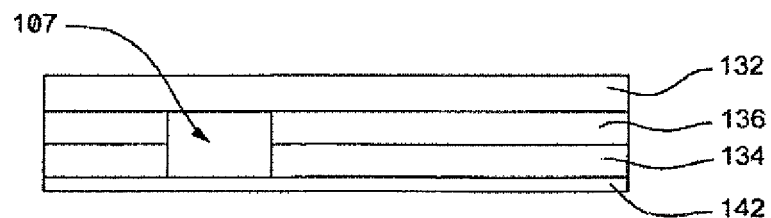
FIG. 5A is a cross-sectional view of the biosensor of FIG. 4 along the line 4A-4A.

FIG. 5A is a cross-sectional view of the biosensor of FIG. 4 along the line 4A-4A. Fill chamber 107 can be formed by removing sections of lower layer 134 and spacer layer 136, but leaving upper layer 132 and sealing layer 142 intact. Sealing layer 142 can be adhered to the outside face of layer 134 and can serve, with the sides of the cut-out sections in layers 134 and 136 and layer 132, to form a capillary channel which is capable of drawing sample into it by capillary action.

Figure 5B:
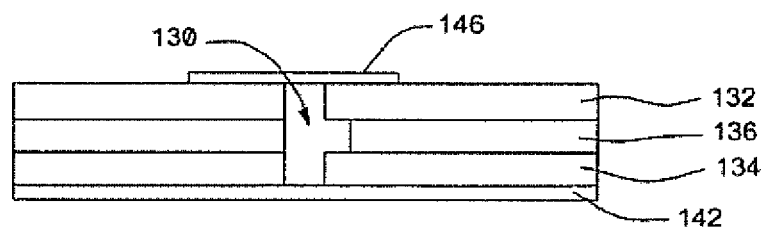
FIG. 5B is a cross-sectional view of the biosensor of FIG. 4 along the line 4B-4B.

FIG. 5B is a cross-sectional view of the biosensor of FIG. 4 along the line 4B-4B. Vent hole 130 can be incorporated into detection chamber 128 by removing sections of or piercing upper layer 132 (or lower layer 134). Layer 146 can be laminated to the upper face of the strip to seal off the opening. Alternatively, if a portion of lower layer 134 is removed, sealing layer 142 can be pierced/removed to open vent hole 130.

Figure 5C:
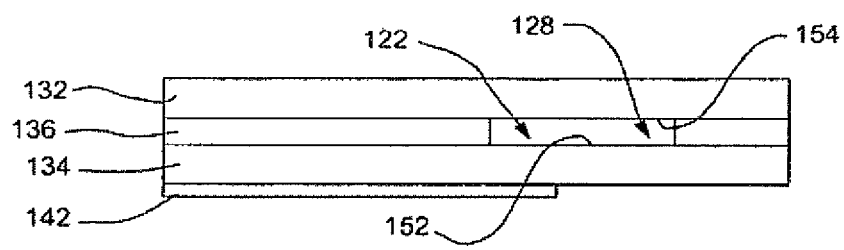
FIG. 5C is a cross-sectional view of the biosensor of FIG. 4 along the line 4C-4C.

FIG. 5C is a cross-sectional view of the biosensor of FIG. 4 along the line 4C-4C. Portions of the electrically conductive film on the upper and lower layers 132, 134 provides electrodes 152, 154 for performing electrochemical reactions. Sealing layer 142 can be adhered to the outside face of layer 134. The portion of the bottom surface of layer 134 which is not covered by layer 142 can provide an electrical contact area which can electrically connect the sensor to a meter. Reaction chamber 122 and detection chamber 128 can be formed by removing a portion of spacer layer 136, but leaving upper 132 and lower layer 134 intact.

Figure 5D:
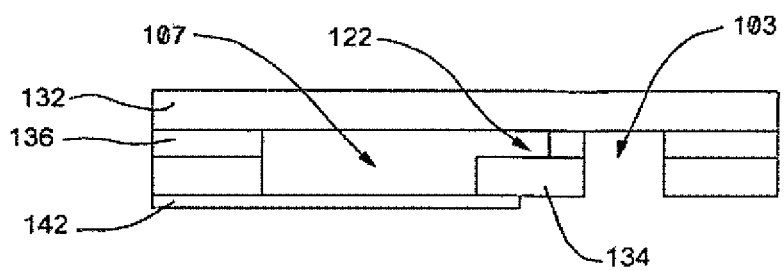
FIG. 5D is a cross-sectional view of the biosensor of FIG. 4 along the line 4D-4D.

FIG. 5D is a cross-sectional view of the biosensor of FIG. 4 along the line 4D-4D. Fill chamber 107 can be formed by removing sections of lower layer 134 and spacer layer 136, but leaving upper layer 132 and sealing layer 142 intact. Sealing layer 142 can be adhered to the outside face of layer 134. Reaction chamber 122 can be defined by removing a section of spacer layer 136, but leaving upper layer 132 and lower layer 134 intact. Contact area 103 can be formed by removing a section of lower layer 134 and spacer layer 136 such that an electrically conductive surface of upper layer 132 is exposed.

Figure 6:
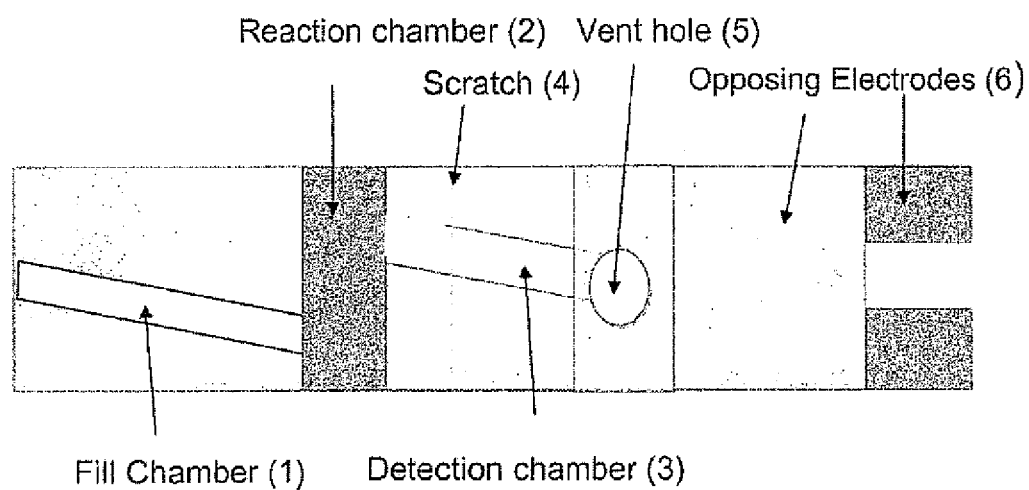
FIG. 6 is a top view of another embodiment of a biosensor disclosed herein.

FIG. 6 is an exemplary embodiment of a biosensor. The biosensor can comprise a fill chamber (1), a reaction chamber (2) and a detection chamber (3). The three chambers are in serial connection in terms of the fluid communication. Scratch (4) can locate near the proximal end of detection chamber (3). Vent hole (5) can locate at the distal end of detection chamber (3). The biosensor can comprise opposing electrodes (6).

Figure 7:
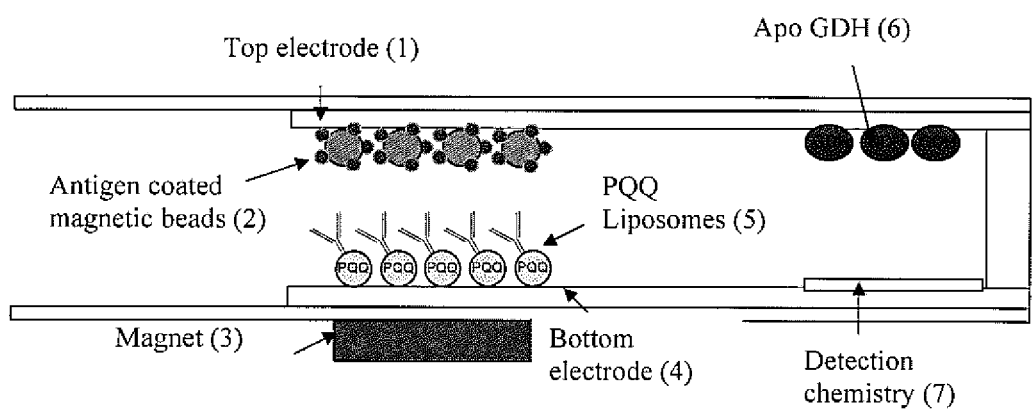
FIG. 7 is a cross-sectional view of the biosensor of FIG. 4 or FIG. 6, illustrating the location of the chemistry.

FIG. 7 is a cross-sectional view of the biosensor of FIG. 4 or FIG. 6, illustrating the location of the chemistry. The reaction chamber can comprise immobilized binding agent molecules on the upper internal surface and probe agent molecules on the bottom internal surface. The top internal surface can be a top electrode (1) which can extend into the detection chamber. The bottom internal surface can comprise a bottom electrode (4) which can extend into the detection chamber. The binding agent can comprise antigen which can be coated on magnetic beads (2). The magnetic beads can be confined within the reaction chamber by a magnet (3) at the bottom of the sensor. The probe agent can comprise PQQ molecules encapsulated within liposomes (5), and binding partners. The detection chamber can comprise apo-GDH (6) on the top internal surface, and other detection chemistry reagents (7) on the bottom internal surface.

A test using the biosensor can use a fluid sample of less than about 100 milliliters, or less than about 50 milliliters, or less than about 20 milliliters, or less than about 10 milliliters, or less than about 5 milliliters, or less than about 3 milliliters, or less than about 2 milliliters, or less than about 1 milliliter, or less than 500 microliters, or less than about 200 microliters, or less than about 100 microliters, or less than about 50 microliters, or less than about 10 microliters, or less than about 1 microliter, or less than about 0.5 microliters, or less than about 0.3 microliters, or less than about 0.1 microliters.

The biosensor can comprise at least one reaction chamber. The reaction chamber can have a proximal end and a distal end. A fluid sample can enter the reaction chamber from the proximal end, and can exit the reaction chamber and/or flow into the detection chamber through the fluid passageway from the distal end.

The reaction chamber can comprise at least one wall which can define the exterior and/or the interior of the reaction chamber. At least one wall of the reaction chamber can comprise a material, such as, for example, polyester, polystyrene, polycarbonate, polyolefin, polyethylene terephthalate, or a mixture thereof. At least one wall of the reaction chamber can comprise a filler, such as, for example, titanium dioxide, carbon, silica, glass, and a mixture thereof.

The reaction chamber can comprise an interior with a volume, at least part of which can be accessible to the fluid sample. The volume can be less than about 100 milliliters, or less than about 50 milliliters, or less than about 20 milliliters, or less than about 10 milliliters, or less than about 5 milliliters, or less than about 3 milliliters, or less than about 2 milliliters, or less than about 1 milliliter, or less than 500 microliters, or less than about 200 microliters, or less than about 100 microliters, or less than about 50 microliters, or less than about 10 microliters, or less than about 1 microliter, or less than about 0.5 microliters, or less than about 0.3 microliters, or less than about 0.1 microliters. The interior of the reaction chamber can comprise a cross-sectional shape of square, rectangular, circular, oval, triangular, rhomboid, trapezoidal, or the like. A cross-section can be perpendicular to the direction of the bulk flow of the fluid sample within the reaction chamber. The cross-sections can be uniform in size and/or shape along the direction of the bulk flow. The cross-sections can be variable along the direction of the bulk flow. Merely by way of example, the cross-sections can taper along the direction of the bulk flow.

The reaction chamber can comprise a capillary distance, $h_1$. The capillary distance can refer to the dimension of the reaction chamber and/or its cross sections which determines the magnitude of the capillary force to the fluid sample. The capillary distance can be the smallest dimension of the interior of the reaction chamber. The magnitude of the capillary force can be inversely related to the capillary distance. The capillary distance can be less than about less than about 1 centimeter, or less than about 5 millimeters, or less than about 2 millimeters, or less than about 1 millimeter, or less than about 500 micrometers, or less than about 200 micrometers, and less than about 100 micrometers, or less than about 50 micrometers. If the biosensor is used by a user who and/or with an apparatus which can generate an external force to transfer the fluid sample between or among different chambers of the device, the device and/or its chambers can comprise a bigger dimension. Merely by way of example, the biosensor can comprise a characteristic length less than about 100 centimeters, or less than about 50 centimeters, or less than about 20 centimeters, or less than about 10 centimeters, or less than about 5 centimeters, or less than about 1 centimeter. As used herein, the characteristic length refers to the diameter of the smallest circle which encloses an entire cross-sectional surface of the reaction chamber.

The interior of the reaction chamber can comprise at least one internal surface. The internal surface(s) can comprise an internal wall/internal walls which can define the cross-sectional shape and/or volume of the interior of the reaction chamber. The internal wall(s) can comprise, but are not limited to, a solid material, a fibrous material, a macroporous material, a powdered material, or the like, or any combination thereof. The internal surface(s) can comprise that/those of at least one independent support within the reaction chamber. A suitable support can comprise, but are not limited to, a solid material, a mesh material, a fibrous material, a porous material, a powdered material, or beads of a material, or a mixture thereof. The mesh material can comprise, for example, a polymer such as polyolefin, polyester, nylon, cellulose, polystyrene, polycarbonate, polysulfone, or a mixture thereof. The fibrous material can comprise, for example, a polymer such as polyolefin, polyester, nylon, cellulose, polystyrene, polycarbonate, polysulfone, or a mixture thereof. The porous material can comprise, for example, a sintered powder, or a macroporous membrane. The macroporous membrane can comprise, for example, a polymeric material such as polysulfone, polyvinylidene difluoride, nylon, cellulose acetate, polymethacrylate, polyacrylate, or a mixture thereof. The bead material can be selected such that suitable support can be provided for an reagent, such as, for example, an binding agent. Suitable beads can comprise those marketed as DYNABEADS® by Dynal Biotech of Oslo, Norway. The beads can comprise, for example, magnetic beads. The support can have at least one of the following benefits. Firstly, it can increase the surface area where the reagents, such as, for example, the binding agent, the probe agent, can attach, and/or where the binding reaction can occur within the reaction chamber. This can decrease the reaction time, and/or the chances for an undesirable process (e.g., contamination, clotting, etc) to occur. Secondly, it can increase the capillary force to the fluid sample by decreasing the capillary distance of the reaction chamber. The reaction chamber can comprise a vent that is open to the atmosphere, thus allowing air displaced by the sample to escape. The fluid sample can be drawn into the reaction chamber until the reaction chamber is filled up to the reaction chamber vent, whereupon filling can stop. The volume of detection chamber can be chosen so as to be roughly equal to and preferably smaller than the volume of the reaction chamber. The volume of the detection chamber can be about 100%, or about 95%, or about 90%, or about 85%, or about 80%, or about 75%, or about 70%, or about 60%, or less than about 50% of that of the reaction chamber.

The reaction chamber can comprise binding agent and probe agent. The relative amounts of the binding agent and the probe agent can be chosen such that there is a slight excess of the binding agent over the probe agent. In this context, a slight excess can be defined to be such that the excess is small when compared to the amount of target analyte to be detected in the fluid sample. For example, the excess can comprise less than about 40%, or less than about 30%, or less than about 25%, or less than about 20%, or less than about 15%, or less than about 10%, or less than about 5%, or less than about 3%, or less than about 2%, or less than about 1% of the average amount of target analyte expected in the fluid sample. The average amount of the target analyte can be estimated, for example, for a population of interest with and/or without a target pathological condition.

The binding agent can be immobilized on at least one internal surface within the reaction chamber so that the binding agent and the species bound to them during the reaction can remain in the reaction chamber and throughout the test. The probe agent can be supported on at least one internal surface within the reaction chamber. The probe agent molecules which are not bound to the immobilized binding agent molecules directly or indirectly can move to the detection chamber with the fluid sample. As used herein, "directly" means that a portion of the probe agent molecule binds to a portion of the binding agent molecule, e.g., a binding site; while "indirectly" means that the probe agent binds to another agent, e.g., the target analyte which binds directly or indirectly to the immobilized binding agent.

The binding agent can be adsorbed or otherwise immobilized onto at least one internal surface of the reaction chamber via chemical bonds. The binding agent can be coated onto beads which can be confined in the reaction chamber throughout a test. Merely by way of example, the beads can be magnetic beads, and the biosensor can comprise a magnetic field to confine the magnetic beads with a coating of binding agent in the reaction chamber. For example, a magnet below the reaction chamber can prevent the transfer of magnetic beads and any species that can be bound to the beads directly or indirectly, such as the binding agent coated on the beads and the probe agent molecules bound to the binding agent molecules. As a result, in an exemplary embodiment, probe agent molecules not bound to the magnetic beads can be measured in the detection chamber. The amount and/or concentration of target analyte in the fluid sample, for example, can be related to the amount/concentration of the probe agent which can be released into the detection chamber.

The probe agent can comprise a binding partner and a vehicle. The binding partner can be bound to the surface of the vehicle. The vehicle can comprise at least one copy of an activating agent. The binding partner can facilitate a probe agent molecule bound to an immobilized binding agent molecule, or to a free target analyte which is not bound to an immobilized binding agent molecule, or to a target analyte which is bound to an immobilized binding molecule. The at least one copy of the activating agent can be surface coated onto or encapsulated within the vehicle.

The probe agent molecules can be supported on at least one internal surface of the reaction chamber. The internal surface of the reaction chamber and the method for coating of the probe agent molecules can be chosen such that only weak bonds between the probe agent molecules and the internal surface can exist. This way the probe agent molecules can be liberated into the sample when the internal surface is wet by the sample. The rate of dissolution of the probe agent molecules from the internal surface can be chosen such that little dissolution has occurred during the time taken for the sample to fill the reaction chamber. In this manner, the probe agent molecules can be evenly distributed throughout the area of the reaction chamber after filling. The internal surface(s) where the probe agent molecules are supported can be the same as, or different from that (those) where the binding agent molecules are immobilized.

In some embodiments, the probe agent molecules can be separate from and/or not bound to the binding agent molecules before a fluid sample fills the reaction chamber and dissolves the probe agent molecules. In some embodiments, after dissolved by the fluid sample in the reaction chamber, the probe agent molecules can bind to the immobilized agent molecules, but with a lower binding affinity compared to the target analyte, to form a competitive assay. The lower binding affinity of a probe agent molecule through its binding partner to an immobilized binding agent molecule can be due to at least one of the following reasons. Firstly, a probe agent molecule can comprise a larger size compared to the target analyte, because of the vehicle linked to the binding partner of the probe agent molecule, and/or the larger size of the binding partner itself than the target analyte. Secondly, the binding partner of a probe agent molecule can be a chemically or otherwise modified version of the target analyte such that the probe agent molecule can bind to the immobilized binding agent molecule through the binding partner, but with decreased binding affinity. The interior binding kinetics of the probe agent molecules can also result from that it can take longer for the probe agent molecules to reach the immobilized binding agent molecules than the target analyte in the fluid sample, because it has to be dissolved first by the fluid sample, and/or because it can move more slowly in the fluid sample due to its larger size than the target analyte. In this manner, the amount/concentration of the target analyte in the fluid sample can be positively related to the amount/concentration of the probe agent released to the detection chamber where the probe agent can be measured qualitatively and/or quantitatively. In other embodiments, after dissolved by the fluid sample in the reaction chamber, the probe agent molecules can bind to the target analyte and form a sandwich assay or a competitive binding assay. A sandwich assay can be formed when a probe agent molecule can bind to a target analyte after the target analyte is bound an immobilized binding agent molecule. In this manner, the amount/concentration of the target analyte in the fluid sample can be inversely related to the amount/concentration of the probe agent molecules released to the detection chamber where the probe agent molecules can be measured qualitatively and/or quantitatively. A competitive binding assay can form if a probe agent molecule, when dissolved by the fluid sample in the reaction chamber, can bind to a free target analyte with a higher binding affinity than it binds to the immobilized binding agent molecule. A free target analyte, as used herein, refers to the target analyte which is not bound to an immobilized binding agent molecule. In this manner, the amount/concentration of the target analyte in the fluid sample can be positively related to the amount/concentration of the probe agent released to the detection chamber where the probe agent molecules can be measured qualitatively and/or quantitatively.

In some embodiments, the probe agent molecules can be bound to the immobilized binding agent molecules when the biosensor is manufactured and/or before a test of a fluid sample using such a biosensor. The binding partner of such a probe agent molecule can comprise a pseudo-analyte, a modified analyte, or the like. As used herein, a pseudo analyte can comprise one which can bind to the immobilized binding agent molecule, but not as strongly as the target analyte. Merely by way of example, if the target analyte is a human protein, then a suitable pseudo-analyte can comprise an animal version of the same protein, such as a dog protein or a pig protein. A modified analyte can comprise one chemically or otherwise modified such that the binding affinity to the binding agent molecule is decreased. The binding affinity of the probe agent molecule to the immobilized binding agent molecule through the binding partner can be lower than that of the target analyte. The lower binding affinity of a probe agent molecule through its binding partner to an immobilized binding agent molecule can be due to at least one of the following reasons. Firstly, a probe agent can comprise a larger size compared to the target analyte, because of the vehicle linked to the binding partner of the probe molecule, and/or the larger size of the binding partner itself. Secondly, the binding partner of a probe agent molecule can be a chemically or otherwise modified version or a different version (e.g. an animal version of a human analyte) of the target analyte such that the probe molecules can bind to the immobilized binding agent molecules through the binding partner, but with decreased binding affinity. After dissolved by the fluid sample in the reaction chamber, the probe agent molecules can be displaced from the binding agent molecules by the target analyte due to the lower binding affinity. In this manner, the amount/concentration of the target analyte in the fluid sample can be positively related to the amount/concentration of the probe agent molecules displaced and released to the detection chamber where the probe agent molecules can be measured qualitatively and/or quantitatively.

A probe agent molecule can comprise a vehicle. In some embodiments, the vehicle can comprise at least one labeling molecule, such as, for example, a radioisotope, a chromophore, or a fluorophore. The vehicle can comprise at least about 10 labeling molecules, or at least about 50 labeling molecules, or at least about 100 labeling molecules, or at least about 200 labeling molecules, or at least about 500 labeling molecules, or at least about 1,000 labeling molecules, or at least about 5,000 labeling molecules, or at least about 10,000 labeling molecules, or at least about 50,000 labeling molecules, or at least about 100,000 labeling molecules. The labeling molecule(s) can be coated on the surface of the vehicle, or encapsulated within the vehicle. The vehicle can comprise a lipidic particle. The labeling molecule(s) can be encapsulated within the lipidic particle. The lipidic particle can comprise one particle selected from a liposome, vesicle, cellular organelle, and the like. The vehicle can comprise a polymer. The activating agent molecules can be bound to the surface of the polymer. The polymer can comprise a dendrimer, or the like.

In other embodiments, the vehicle can comprise at least one copy of an activating agent. The vehicle can comprise a plurality copies of an activating agent. The vehicle can comprise at least about 5 copies, or at least about 10 copies, or at least about 50 copies, or at least about 100 copies, or at least about 200 copies, or at least about 500 copies, or at least about 1,000 copies, or at least about 5,000 copies, or at least about 10,000 copies, or at least about 50,000 copies, or at least about 100,000 copies of an activating agent. The activating agent molecules can be coated on the surface of the vehicle, or encapsulated within the vehicle. The vehicle can comprise a lipidic particle. The activating agent molecules can be encapsulated within the lipidic particle. The lipidic particle can comprise one particle selected from a liposome, vesicle, cellular organelle, and the like. The vehicle can comprise a polymer. The activating agent molecules can be bound to the surface of the polymer. The polymer can comprise a dendrimer, or the like.

An activating agent molecule can activate a detection agent molecule in the detection chamber such that a signal can be generated and detected. Merely by way of example, the detection agent can comprise an enzyme, and the activating agent can comprise a cofactor which can activate the enzyme. As a more specific example, the detection agent can comprise an apo-enzyme, and the activating agent can comprise the corresponding cofactor. The apo-enzyme and cofactor pair can comprise apo-glucose oxidase and flavin adenine dinucleotide. The apo-enzyme and cofactor pair can comprise apo-glucose dehydrogenase and PQQ.

The reaction chamber can comprise other agents besides the binding agent and the probe agent, such as, for example, a blocking agent, an unactivated agent, or any combination thereof.

The blocking agent can block non-specific binding of an agent onto the immobilized binding agent, the probe agent, and/or the internal surface(s) within the reaction chamber. The agent can comprise at least one present in the fluid sample to be tested, such as, for example, a protein or a lipidic particle. The lipidic particle can be at least one selected from a liposome, a vesicle, a cellular organelle, and the like. The blocking agent can comprise at least one agent selected from a blocking protein and a surfactant. The blocking protein can comprise, for example, bovine serum protein. A nonionic surfactant may also be used as such an agent, e.g., TRITON™ X-100 (a polyoxyethylene octyl phenyl ether) manufactured by Rohm & Haas of Philadelphia, Pa., or TWEEN® manufactured by ICI Americas of Wilmington, Del. In some embodiments, the nonionic surfactant selected does not denature proteins. The blocking agent can be coated onto any internal surface(s) of the reaction chamber, comprising where the binding agent molecules are immobilized, and/or where the probe agent molecules are supported, and/or where neither of the binding agent molecules nor the probe agent molecules are coated. The blocking agent and the agents bound to them can be confined in the reaction chamber during a test. This can be achieved by any of the methods by which binding agent molecules can be immobilized in the reaction chamber. Merely by way of example, the binding agent can be absorbed onto a porous internal surface of the reaction chamber.

The unactivated agent can bind to an unbound or unencapsulated activating agent. This can prevent an unbound or unencapsulated activating agent from moving to the detection chamber and activating a detection agent in a manner independent of the presence of the target analyte in the fluid sample, which can deteriorate the accuracy and/or validity of a test. As used herein, "unbound" or "unencapsulated" means not bound to, encapsulated within, otherwise integral to the vehicle when the vehicle (and the probe agent) is within the reaction chamber and/or before the vehicle (and the probe agent) moves to the detection chamber with the reacted fluid sample. This can result from a vehicle of the probe agent which can become leaky, or rupture, or desorb activating agent molecules during manufacture, storage, or during a test under certain conditions, such as pH, temperature, etc. The unactivated agent can comprise any agent which can bind to the unbound or unencapsulated activating agent. For example, if the activating agent comprise a cofactor which can bind to an apo-enzyme, the unactivated agent can comprise the apo-enzyme. The unactivated agent molecules can be immobilized on an internal surface of the reaction chamber. Therefore, the activating agent molecules bound to them can be confined in the reaction chamber during a test. This can reduce the amount of the unbound or unencapsulated activating agent molecules that can move to the detection chamber in a manner independent of the present and/or the amount of the target analyte in a fluid sample. The unactivated agent molecules can be immobilized by any of the methods by which binding agent molecules can be immobilized in the reaction chamber. Merely by way of example, the unactivated agent molecules can be immobilized within the reaction chamber by binding them to magnetic beads, and the magnetic beads can be confined within the reaction chamber by a magnetic field.

The reaction chamber can comprise a buffer which can adjust the pH of the fluid sample, for example, in the reaction chamber. The buffer can stabilize as least one of the reagents in the reaction chamber during manufacture and/or storage. The buffer can comprise a substance selected from phosphate, citrate, citraconate, mellitate, tris, pipes, mops, hepes, phthalate, imadazole.

The reaction in the reaction chamber can take from about 0.1 seconds to about 60 minutes, or from about 1 second to about 30 minutes, or from about 10 seconds to about 25 minutes, or from about 20 seconds to about 20 minutes, or from about 30 seconds to about 15 minutes, or from about 1 minute to about 10 minutes, or from about 2 minutes to about 8 minutes, or from about 3 minutes to about 5 minutes.

The device can comprise at least one detection chamber. The detection chamber can have a proximal end and a distal end. After a fluid sample finishes the reaction within the reaction chamber, the reacted fluid sample exiting the reaction chamber from the distal end of the reaction chamber can enter the detection chamber from its proximal end through the sample passageway. The detection chamber can be configured such that it can detect a signal generated in the detection chamber in a manner dependent on the presence and/or the amount of the probe agent molecules that transfer to the detection chamber.

The detection chamber can comprise at least one wall which can define the exterior and/or the interior of the detection chamber. At least one wall of the detection chamber can comprise a filler. The design of the at least one wall and the filler of the detection chamber can be similar to those of the reaction chamber.

The detection chamber can comprise an interior with a volume, at least part of which can be accessible to the fluid sample. The volume can be less than about 100 milliliters, or less than about 50 milliliters, or less than about 20 milliliters, or less than about 10 milliliters, or less than about 5 milliliters, or less than about 3 milliliters, or less than about 2 milliliters, or less than about 1 milliliter, or less than 500 microliters, or less than about 200 microliters, or less than about 100 microliters, or less than about 50 microliters, or less than about 10 microliters, or less than about 1 microliter, or less than about 0.5 microliters, or less than about 0.3 microliters, or less than about 0.1 microliters. The interior of the detection chamber can comprise a cross-sectional shape of square, rectangular, circular, oval, triangular, rhomboid, trapezoidal, or the like. A cross-section can be perpendicular to the direction of the bulk flow of the fluid sample within the detection chamber. The cross-sections can be uniform in size and/or shape along the direction of the bulk flow. The cross-sections can be variable along the direction of the bulk flow. Merely by way of example, the cross-sections can taper along the direction of the bulk flow.

The detection chamber can comprise a capillary distance, $h_2$. The magnitude of the capillary force can be inversely related to the capillary distance. The capillary distance can be less than about less than about 1 centimeter, or less than about 5 millimeters, or less than about 2 millimeters, or less than about 1 millimeter, or less than about 500 micrometers, or less than about 200 micrometers, and less than about 100 micrometers, or less than about 50 micrometers. The capillary distance of the detection chamber $h_2$ can be smaller than that of the reaction chamber, $h_1$. If the biosensor is used by a user who and/or with an apparatus which can generate an external force to transfer the fluid sample between or among different chambers of the device, the device and/or its chambers can comprise a bigger dimension. As used herein, the external force does not include the force generated by a user to open the vent in the detection chamber. Merely by way of example, the device can comprise a characteristic length less than about 100 centimeters, or less than about 50 centimeters, or less than about 20 centimeters, or less than about 10 centimeters, or less than about 5 centimeters, or less than about 1 centimeter. As used herein, the characteristic length refers to the diameter of the smallest circle which encloses an entire cross-sectional surface of the detection chamber.

The interior of the detection chamber can comprise at least one internal surface. The internal surface(s) can comprise an internal wall/internal walls which can define the cross-sectional shape and/or volume of the interior of the detection chamber. The internal surface(s) can comprise that/those of at least one independent support within the detection chamber. The internal wall(s) and/or the independent support of the detection chamber can be similar to that/those of the reaction chamber.

The detection chamber can comprise a vent that can be open to the atmosphere. The vent can reside at the distal end of the detection chamber. An exemplary configuration is shown as vent 30 in FIG. 2 and vent 130 in FIG. 4. The vent can be initially closed. This way, when the reaction chamber fills with a fluid sample, the sample passageway to the detection chamber can be blocked by a pneumatic pressure generated by the air trapped within the detection chamber. This pneumatic pressure can substantially prevent the fluid sample from filling the detection chamber. A small amount of sample can enter the detection chamber during the time between when the sample first contacts the sample passageway to the detection chamber and when the sample contacts the far side of the sample passageway. When the sample has wet totally across the sample passageway to the detection chamber, filling of the detection chamber can stop. The volume of the reaction chamber can be chosen so as to be at least equal to and preferably larger than the volume of the detection chamber. By opening the vent in the detection chamber to the atmosphere, sample can be transferred to fill the detection chamber. The vent can be opened by such as, for example, piercing the device, and/or removing an outer layer, and/or tearing a portion of the device (i.e., tearing along a perforation). Merely by way of example, the vent can be opened using a needle controlled by a user or a solenoid in the meter which is connected to the device. Opening the vent can allow air displaced by the sample and trapped within the detection chamber to escape, and therefore, can reduce the pneumatic pressure which can prevent the fluid sample from filling the detection chamber. The device can be configured such that the capillary force to the fluid sample in the detection chamber is higher than that present in the reaction chamber. The increased capillary force can be provided by suitably coating the internal surfaces of the reaction chamber and of the detection chamber, and/or, by choosing the capillary distance for the detection chamber $h_2$ to be smaller than that of the reaction chamber $h_1$. This way, the fluid sample can be drawn into the detection chamber simply by opening the vent, without requiring any other external force generated by the user, or by an external device, such as, for example, a pump or a syringe. In other embodiments, the filling of the detection chamber by the (reacted) fluid sample can be controlled by an external force generated by a user or an external device, such as, for example, a pump, a syringe, or any combination thereof. An external force can also be supplied as a supplementary force to move the fluid sample from the reaction chamber to the detection chamber in addition to the capillary force. As used herein, the external force does not include the force generated by a user to open the vent in the detection chamber by, for example, piercing.

The probe agent molecules can be transferred to the detection chamber with the reacted fluid sample. The presence of the probe agent molecules in the detection chamber can be detected qualitatively and/or quantitatively by signals generated by labeling molecules, such as, for example, radioisotopes, chromophores, or fluorophores. At least one wall of the detection chamber can be permeable to the signals generated by such labeling molecules. Merely by way of example, at least one detection chamber wall can be transparent to a radiation emitted or absorbed by the radioisotopes, and the radiation can be indicative of a presence or absence of the probe agent molecules in the detection chamber.

The presence of the probe agent molecules in the detection chamber can be detected qualitatively and/or quantitatively by an electrochemical reaction. In such embodiments, the detection chamber can comprise an electrochemical cell which can comprise at least two opposing electrodes, at least one sensing/working electrode and at least one counter/reference electrode. The step of determining the presence of the probe agent molecules in the reacted fluid sample can comprise: applying a potential between the sensing/working electrode and the counter/reference electrode in the electrochemical cell; and measuring a current, wherein the current can be a qualitative and/or quantitative indication of the probe agent in the reacted fluid sample in the detection chamber, which can be a qualitative and/or quantitative indication of the target analyte in the fluid sample.

The sensing electrode can be sensitive to the amount of reduced redox agent in the antioxidant case or oxidized redox agent in the oxidant case. In the case of a potentiometric sensor wherein the potential of the sensing electrode is indicative of the level of analyte present, at least one other electrode can act as a reference electrode to provide a reference potential. In the case of an amperometric sensor wherein the sensing electrode current is indicative of the level of analyte in the sample, at least one other electrode can act as a counter electrode to complete the electrical circuit, and/or a reference electrode. Alternatively, the counter electrode and the reference electrode can be two separate electrodes.

At least one of the electrodes can comprise an electrically conductive material, such as, for example, aluminum, copper, nickel, chromium, steel, stainless steel, palladium, platinum, gold, iridium, carbon, carbon mixed with binder, indium oxide, tin oxide, a conducting polymer, or a mixture thereof. The cathode in the electrochemical cell can comprise an electrically conductive material, such as, for example, aluminum, copper, nickel, chromium, steel, stainless steel, platinum, palladium, carbon, carbon mixed with a binder, indium oxide, tin oxide, mixed indium/tin oxides, gold, silver, iridium, a conducting polymer, or the like, or a mixture thereof. The conducting polymer can comprise, such as, for example, polypyrrole or polyacetylene, or the like, or a combination thereof. The anode in the electrochemical cell and/or the electrode(s) which can come into contact with oxidizing substances during device manufacture or storage, can comprise at least one electrically conductive material, such as, for example, platinum, palladium, carbon, carbon mixed with a binder, indium oxide, tin oxide, mixed indium/tin oxides, gold, silver, iridium, a conducting polymer, or the like, or a mixture thereof. The conducting polymer can comprise, such as, for example, polypyrrole or polyacetylene, or the like, or a combination thereof. Materials suitable for use as electrodes can be compatible with the reagents present in the device, namely, they do not react chemically with the reagents at the potential of choice, and/or during sensor fabrication, and/or storage, and/or usage. The opposing electrodes can comprise the same conductive material, or different materials.

The sensing/working electrode and the counter/reference electrode can reside on at least one internal surface of the detection chamber. The opposing electrodes can be electrically insulated to each other before the detection chamber is filled with the fluid sample. The insulation can be achieved by separating the two opposing electrodes with an electrically insulating material, or by creating a break on an electrically conductive layer or film. The opposing electrodes reside on the same internal surface or different internal surfaces of the detection chamber. The opposing electrodes can be separated by about 5 micrometers, or about 10 micrometers, or about 15 micrometers, or about 20 micrometers, or about 25 micrometers, or about 30 micrometers, or about 35 micrometers, or about 40 micrometers, or about 45 micrometers, or about 50 micrometers, or about 75 micrometers, or about 100 micrometers, or about 125 micrometers, or about 150 micrometers, or about 175 micrometers, or about 200 micrometers, or about 250 micrometers, or about 300 micrometers, or about 350 micrometers, or about 400 micrometers, or about 450 micrometers, or about 500 micrometers, or about 600 micrometers, or about 700 micrometers, or about 800 micrometers, or about 900 micrometers, or about 1 millimeter, or greater than about 2 millimeters, or greater than about 3 millimeters, or greater than about 4 millimeters, or greater than about 5 millimeters. In terms of the relative position, the opposing electrodes can be in a parallel opposing relationship, or a side-by-side relationship, or a parallel but offset relationship, or a coplanar relationship. The opposing electrodes can be identical or substantially similar in size, or can be of different sizes and/or different shapes.

The device can comprise more than two electrodes. Merely by way of example, the device can comprise a third electrode which can be a counter/reference electrode. The two counter/reference electrodes can be electrically connected. The third electrode can form a circuit with the sensing/working electrode which can detect the filling of the reaction chamber and/or the detection chamber. Merely by way of example, the filling of the reaction chamber detected this way can be used as a signal to activate a timing device such that the reaction time can be controlled and/or a following step of a test, such as, for example, transferring the reacted fluid sample to the detection chamber, can be triggered after a per-determined amount of time. As another example, if the device comprises two detection chambers, each detection chamber can comprise one counter/reference electrode, and the two detection chambers can share one sensing/working electrode extending to both detection chambers. In such embodiments, two electrical signals can be obtained in one test.

Other variations in electrode configuration, spacing, and construction or fabrication would be within the scope of the disclosure.

At least a portion of one of the internal surface of the detection chamber can comprise a conductive layer or film which can be electrically connected to but extended beyond the electrodes. The extended conductive layer or film can be used as a contact area where the device is electrically connected to another device, such as, for example, a meter. In certain embodiments, the detection chamber can comprise two internal surfaces which comprise conductive films and/or are electrically connected to the opposing electrodes, but electrically insulated to each other. As used herein, "substantially" means that at least about 30%, or at least about 40%, or at least about 50%, or at least about 60%, or at least about 70%, or at least about 80%, or at least about 90%, or at least about 95% of either of the two internal surfaces are coated with electrically conductive material. Each electrically conductive film can be continuous or patterned. For example, the patterned conductive film can form two electrodes which are conductive to each other; or an electrode and a contact area, wherein the contact area can electrically connect the electrode to an external device, such as, for example, a meter.

There can be a scratch on at least on of the internal surface of the detection chamber. An exemplary illustration can be Scratch 106 in FIG. 4. The scratch can generate a break in the electrically conductive film within the detection chamber. The break can be affected by patterning the conductive film when it is laid down or by creating the break during manufacture. Scratch 106 can be affected by scratching the film, scraping part of the film away, chemically etching the conductive layer or film, laser ablating the conductive layer or film or other methods. Scratch 106 in the conductive layer or film can serve to, in part, define the active electrode area of the detection chamber by electrically isolating the conductive coated in the detection chamber from that in the reaction chamber. This can be advantageous as it can prevent any electric signal that can otherwise flow at the conductive layers or films in the reaction chamber from effecting the test results. The scratch can be wide enough to reliably break the electrical conduction of the layer where the scratch reside, but not so wide as to prevent fluid from crossing it, such as, for example, under capillary action. The scratch can be from about 1 micrometer to 10 millimeters, preferably from about 10 micrometers to about 1 millimeter, and most preferably from about 20 micrometers to about 200 micrometers. The distance between the scratch and the proximal end of the detection chamber can be about 1%, or about 5%, or about 10%, or about 15%, or about 20%, or about 25%, or about 30%, or about 35%, or about 40%, or about 45%, or about 50%, or greater than 55% of the distance between the proximal end and the distal end of the detection chamber.

At least one internal surface of the detection chamber can be coated with detection agent. The detection agent can be dissolved by and/or diffusible in the fluid sample in the detection chamber, and can be coated on any internal surface of the detection chamber. In some embodiments, the detection agent cannot be dissolved by or diffusible in the fluid sample. Such a detection agent can be coated in the vicinity of where the detection can be made. As used herein, "vicinity" means within the distance across which the detection agent or the derivative of them can be detected by, such as, for example, the electrodes. The derivative of the detection agent means a species generated and/or activated by the reaction of the detection agent with a species carried to the detection chamber by the probe agent, for example, the activating agent. The detection agent can comprise an enzyme, such as, for example, a glucose oxidase, a glucose dehydrogenase. The detection agent can comprise a species which can be activated by an activating agent surface bound onto or encapsulated within a probe agent molecule carried to the detection chamber by the fluid sample. The detection agent and activating agent pair can comprise, an apo-enzyme and its cofactor. Merely by way of example, the detection agent and activating agent pair can comprise apo-glucose oxidase and flavin adenine dinucleotide; the detection agent and activating agent pair can comprise apo-glucose dehydrogenase and PQQ. If one copy of the target analyte present in the fluid sample corresponds to one probe agent molecule comprising multiple copies of an activating agent transferred to the detection chamber, and one copy of the activating agent can activate one detection agent molecule to generate a unit of signal, then one copy of the target analyte can correspond to multiple units of signal. This can increase the sensitivity, and/or accuracy, and/or rate of the test.

The detection chamber can comprise a liberating agent which can liberate the activating agent molecules from the vehicle of a probe agent molecule such that the activating agent molecules can react with and activate the detection agent molecules. The liberating agent can comprise at least one selected from a mild detergent, a lytic peptide, an enzyme, heating, cooling, ultrasonication, a light source together with a photochemically activated lysing agent, or the like, or any combination thereof. The mild detergent can comprise at least one selected from n-octyl-B-D-glucopyranoside, TWEEN® 20 (Polysorbate 20), BRIJ® 35 (polyethylene glycol lauryl ether) and TRITON™ X-100 (a polyoxyethylene octyl phenyl ether). The peptide can comprise at least one selected from mellitin, and one of a class of phospholipases, a component of the complement system. The enzyme can comprise at least one selected from protease and trypsin. The liberating agent can comprise physical means of releasing the activating agent molecules from the vehicle. There can comprise heating or cooling, ultrasonication or a combination of physical and chemical means, such as, for example, a photochemical reaction initiated by a light source directed into the sensor. The liberating agent can be dissolved by and/or diffusible in the fluid sample in the detection chamber, and can be coated on any internal surface of the detection chamber.

If the detection agent or its derivative is an enzyme, the detection chamber can comprise an enzyme substrate which can react with the detection agent or its derivative to produce a detectable signal. An exemplary illustration is enzyme substrate 64 in FIG. 3. The enzyme substrate can be of sufficient amount such that the rate of reaction of the detection agent or its derivative present with the enzyme substrate is determined by the amount of detection agent or its derivative present in the detection chamber. The enzyme substrate can comprise an oxidizable substrate. The oxidizable substrate can comprise one substrate selected from galactose, maltose, xylose, and acetic acid. For instance, if the detection agent or its derivative is glucose oxidase or glucose dehydrogenase, the enzyme substrate can comprise glucose.

The detection chamber can comprise at least one mediator which can react with the detection agent or its derivative to produce a detectable signal. The mediator can be of sufficient amount such that the rate of reaction of the detection agent or its derivative present with the enzyme substrate is determined by the amount of detection agent or its derivative present in the detection chamber. In an embodiment wherein an electrochemical detection system is used, ferricyanide can be a suitable mediator. Other suitable mediators can comprise one selected from dichlorophenolindophenol, and complexes between transition metals and nitrogen-containing heteroatomic species. The detection chamber can comprise two or more mediators which can increase the rate of a detection reaction in certain embodiments.

The detection chamber can comprise a buffer which can adjust the pH of the fluid sample, for example, in the detection chamber. The buffer can stabilize as least one of the reagents in the detection chamber during manufacture and/or storage. The buffer can comprise a substance selected from phosphate, citrate, citraconate, mellitate, tris, pipes, mops, hepes, phthalate, imadazole.

The enzyme substrate, and/or the mediator, and/or the buffer reagents can be present in sufficient quantity/quantities such that the rate of reaction of the detection agent or its derivative with the enzyme substrate is limited by the amount of the detection agent or its derivative present in the detection chamber.

There can be a sample passageway between a pair of chambers through which the fluid sample can flow from one chamber to the other. For example, there can be a sample passageway 38 between the reaction chamber and the detection chamber, as illustrated in FIG. 2. The flow through the fluid passageway can be controlled by a force balance via, such as, for example, a capillary action, a pneumatic pressure, an external force, or the like, or any combination thereof. The fluid passageway can comprise an open passageway. The fluid passageway can comprise an entity. The entity can be semipermeable and/or can allow the passage of certain species and block the others based on, for example, size, charge, osmolarity, or the like, or any combination thereof. Merely by way of example, such an entity can provide a mechanism to confined certain species within the reaction chamber. The sample passageway can comprise a cross-sectional shape of square, rectangular, circular, oval, triangular, rhomboid, trapezoidal, or the like. A cross-section can be perpendicular to the direction of the bulk flow of the fluid sample from the reaction chamber to the detection chamber. The cross-sections can be uniform in size and/or shape along the direction of the bulk flow. The cross-sections can be variable along the direction of the bulk flow. Merely by way of example, the cross-sections can taper along the direction of the bulk flow. The fluid passageway can comprise a capillary distance. The capillary distance can be between those of the two chambers it connects. It can allow for a fluid sample to flow from one chamber to the other through the fluid passageway via capillary action alone, i.e., in the absence of an external force. As used herein, an external force does not include the force generated by a user to open the vent in the detection chamber by, for example, piercing. For example, in some embodiments, the fluid sample can transfer from one chamber to the other upon opening the vent at the distal end of the detection chamber by, for example, piercing. The capillary force can be manipulated by, for example, the coating on at least one of the internal surface of the fill chamber. If the biosensor is configured to use an external force generated by a user or an apparatus, such as, for example, a pump, syringe, or the like, the capillary distance of the fluid passageway can be larger or smaller than either of those of the chambers it connects.

The device can comprise a fill chamber. An exemplary illustration can be Fill Chamber 107 in FIG. 4. The fill chamber can comprise at least one internal surface. The fill chamber can comprise at least one wall which can define the exterior and/or the interior of the reaction chamber. The fill chamber can comprise an interior with a volume, at least part of which can be accessible to the fluid sample. The volume can be less than about 100 milliliters, or less than about 50 milliliters, or less than about 20 milliliters, or less than about 10 milliliters, or less than about 5 milliliters, or less than about 3 milliliters, or less than about 2 milliliters, or less than about 1 milliliter, or less than about 500 microliters, or less than about 200 microliters, or less than about 100 microliters, or less than about 50 microliters, or less than about 10 microliters, or less than about 1 microliter, or less than about 0.5 microliters, or less than about 0.3 microliters, or less than about 0.1 microliters.

The interior of the fill chamber can comprise a cross-sectional shape of square, rectangular, circular, oval, triangular, rhomboid, trapezoidal, or the like. A cross-section can be perpendicular to the direction of the bulk flow of the fluid sample within the fill chamber. The cross-sections can be uniform in size and/or shape along the direction of the bulk flow. The cross-sections can be variable along the direction of the bulk flow. Merely by way of example, the cross-sections can taper along the direction of the bulk flow.

The fill chamber can comprise a capillary distance. A fluid sample can be drawn into the fill chamber. The capillary distance can be larger than that of the reaction chamber. It can allow for a fluid sample to flow from the fill chamber to the reaction chamber via capillary action alone, i.e., in the absence of an external force. As used herein, an external force does not include the force generated by a user to open the vent in the detection chamber by, for example, piercing. For example, in some embodiments, the fluid sample can transfer from one chamber to the other upon opening the vent at the distal end of the detection chamber by, for example, piercing. The capillary force can be manipulated by, for example, the coating on at least one of the internal surface of the fill chamber. If the biosensor is configured to use an external force generated by a user or an apparatus, such as, for example, a pump, syringe, or the like, the capillary distance of the fill chamber can be smaller than that of the reaction chamber.

At least one internal surface of the fill chamber can be coated with a blocking agent. The blocking agent in the fill chamber can be similar to that in the reaction chamber. At least one internal surface of the fill chamber can be coated with a buffer. The buffer can be similar to that in the reaction chamber and/or in the detection chamber.

The biosensor can comprise at least one sealing layer which can prevent leakage of fluid and/or electrical signal. Exemplary materials for a sealing layer can comprise, for example, plastics (e.g. PET, PETG, polyimide, polycarbonate, and/or polystyrene), silicon, ceramic, glass, and any combination thereof. A sealing layer can comprise, or be formed substantially of, an adhesive. If the detection chamber comprises an electrochemical cell, a sealing layer positioned adjacent to at least one of the electrodes and/or the electrically conductive layers or films. A sealing layer can be positioned adjacent to at least one of the first and second electrically conductive layers or films. The sealing layer can be positioned over the vent hole at the distal end of the detection chamber to provide a cover for the pre-formed vent hole. In some embodiments, a porting of the sealing layer can be removing by, for example, piercing, to create the vent hole where trapped air can escape from a chamber of the biosensor. A sealing layer can be configured such that a portion of the conductive layer or film can be exposed to form a contact area where the biosensor can be electrically connected to a meter. Such configuration can comprise that the sealing layer can have a smaller area than that of the conductive layer or film, and/or that the sealing layer can be positioned so that it does not cover the entire conductive layer or film.

Method of Manufacture

Merely for the purpose of convenience, methods of manufacturing a biosensor as described herein are described in terms of several exemplary embodiments. However, it is understood that it is for illustration purpose only, and is not intended to limit the scope of the disclosure.

The biosensor 20, illustrated in FIGS. 2 and 3, comprises a detection chamber 28 comprising an electrochemical cell and a reaction chamber 22 containing immobilized binding agent molecules and probe agent molecules. The detection chamber 28 and reaction chamber 22 can be prepared by forming an aperture extending through a sheet of electrically resistive spacer material 36. The aperture can be shaped such that it defines a sidewall of both the reaction chamber 22 and detection chamber 28, as well as a sample passageway 38 between chambers 22, 28. By extending the aperture from a proximal end 24 of reaction chamber 22 through to an edge 37 of sensor 20, a sample ingress 25 can be formed. In one embodiment, the thickness of sheet 36 can define the height of the reaction chamber 22 and detection chamber 28, and the chambers can have an equal height. According to this embodiment the capillary force in the detection chamber can be greater than that in the reaction chamber. This can be achieved by modifying the surfaces of the reaction chamber and/or detection chamber or by adding filling materials, such as those herein disclosed, to the detection chamber.

In another embodiment, the height of reaction chamber 22 can be greater than that of detection chamber 28. A reaction chamber 22 of greater height than detection chamber 28 can be prepared, for example, by layering multiple inner sheets 32, 34, 36 and/or outer sealing sheets 42, 46 together. For example, in FIG. 3 the middle sheet 36 of sensor 20 has an aperture defining the sidewalls of reaction chamber 22 and detection chamber 28 as described above. Middle sheet 36 can then be sandwiched between one or more additional layers 32, 34, the additional layers 32 and 34 having an aperture corresponding only to reaction chamber 22. With respect to detection chamber 28, layers 32 and 34 define the end walls 60, 62 (i.e., top and bottom surfaces) of the chamber. In this embodiment, the end walls 60 and 62 of the detection chamber comprise electrodes 54 and 52, electrically connectable, via connection means, to a measuring circuit. The electrodes are described in more detail below.

In one aspect, the electrodes 52 and 54 can be placed in electrical connection with a meter (not shown) through the connection end 66. The connection end can allow a meter (not shown) to electrically communicate with the electrodes 52 and 54 in the detection chamber 28 via electrically conductive tracks (not shown). The meter in connection with the connection area 66 can apply a potential between the electrodes 52 and 54 in the detection chamber 28 and detecting the electrical signals generated during an electrochemical reaction.

The biosensor 120, illustrated in FIGS. 4, 5 and 7, or the biosensor illustrated in FIG. 6, comprises three chambers. The sensor can include a fill chamber 107 in addition to a reaction chamber 122 and a detection chamber 128. Sensor 120 can be formed from multiple layers as described above, including for example, a sealing layer 142, a lower layer 134, a spacer layer 136, and an upper layer 132. In one aspect, each layer can comprise an insulating material, while upper and lower layers 132, 134 additionally include an electrically conductive film as discussed in more detail below. By removing portions of the layers at different points in the sensor, a fill chamber 107, reaction chamber 122, and a detection chamber 128 are formed. In addition, exposing portions of the electrically conductive film on the upper and lower layers 132, 134 provides electrodes 152, 154 for performing electrochemical reactions and provides electrical contact areas 101, 102, 103 for electrically connecting the sensor to a meter.

Contact area 101, for electrically contacting a lower layer 134 carrying the lower conductive film, can be formed by extending lower layer 134 out past the end of a spacer layer 136 and the upper layer 132. Contact area 102 can be formed by removing sections of layers 134 and 136 to expose a section of upper layer 132. Contact area 103 can be similarly formed by removing a section of lower layer 134 and spacer layer 136 as shown in FIG. 5D (cross-section D-D' in FIG. 4).

Fill chamber 107 can be formed by removing sections of lower layer 134 and spacer layer 136, but leaving upper layer 132 and sealing layer 142 intact. Sealing layer 142 can be adhered to the outside face of layer 134 and can serve, with the sides of the cut-out sections in layers 134 and 136 and layer 132, to form a capillary channel which is capable of drawing sample into it by capillary action. This channel is illustrated in FIG. 5A (cross-section A-A' in FIG. 4).

Reaction chamber 122 can be formed by removing a section of the spacer layer 136 but leaving layers 134 and 132 intact. This can form a capillary space where the height of the capillary spacer is smaller than the height of the filling chamber 122. This can allow to draw liquid from the filling chamber 122 into the reaction chamber 128 by capillary action. The small height of the reaction chamber can allow for relatively rapid mixing of components in the reaction chamber. In one aspect, reaction chamber 122 can open at the lateral edge(s) of the strip to allow air to vent while liquid fills the reaction chamber.

Detection chamber 128 can be formed in a similar fashion to the reaction chamber 122 by removing a section of the spacer layer 136 while leaving the layers 134 and 132 intact. Initially, the detection chamber 128 can open to the reaction chamber 122 at one end but has no other opening.

Vent hole 130 can be incorporated into the detection chamber 128 by removing sections of or piercing upper layer 132 (or lower layer 134), A layer 146 shown in FIG. 5B (cross-section B-B' in FIG. 4) can be laminated to the upper face of the strip to seal off the opening. Alternatively, if a portion of lower layer 134 is removed, sealing layer 142 can be pierced/removed to open vent hole 130.

In one aspect, the electrically conductive film defining electrodes 52, 152, 54, 154 can be adhered to a surface the immunosensor by means of an adhesive. Suitable adhesives can comprise, for example, heat activated adhesives, pressure sensitive adhesives, heat cured adhesives, chemically cured adhesives, hot melt adhesives, hot flow adhesives, and the like. In an alternative aspect, the electrically conductive film can be prepared by coating (e.g., by sputter coating or screen printing) a sheet of electrically resistive material with a suitable electrically conductive material, for example, platinum, palladium, carbon, indium oxide; tin oxide, mixed indium/tin oxides, gold, silver, iridium, mixtures thereof, and the like. Materials suitable for use as the electrodes can be compatible with the reagents present in the sensor 20, 120. Suitable electrically resistive materials include, for example, polyesters, polystyrenes, polycarbonates, polyolefins, mixtures thereof, and the like.

Scratch 106 in FIG. 4 denotes a break in the electrically conductive film defining upper electrode 154 on upper layer 132. The break can be affected by patterning the conductive film when it is laid down or by creating the break during manufacture. Scratch 106 can be affected by scratching the film, scraping part of the film away, chemically etching the film, laser ablating the film or other methods as commonly known.

Methods for making numerous types of liposome with different functionalities and small molecule inclusions are well known in the literature. For exmaple, see Liposomes: A Practical Approach (Second Edition, Editors: VA Torchilin and V Weissig, Oxford University 2003). Alternative antibody can be added indirectly. For example, a biotinlyated lipid such as Biotin DHPE (N-(biotinoyl)-1,2-dihexadecanoyl-sn-glycero-3-phosphoethanolamine), can be incorporated into the liposome, then streptavidin or avidin added and then finally a biotinlyated antibody. In addition, methods are known for construction of polymers with small molecule attachment. For example, see "In Vitro Targeting of Synthesized Antibody-Conjugated Dendrimer Nanoparticles" by Thomas et al. (*Biomacromolecules*, 5(6): 2269-2274, Nov. 8, 2004).

Reagents for use in the biosensor, e.g., immobilized antibody/antigen, probe-linked antigen/antibody, buffer, mediator, enzyme substrate, and the like, can be supported on the walls the reaction chamber 22, 122 or on an independent support contained within chambers, within a matrix, or can be self supporting. If the reagents are to be supported on the internal chamber walls or the electrodes, the chemicals can be applied by use of printing techniques, e.g., ink jet printing, screen printing, lithography, and the like. In an alternative embodiment, a solution containing the reagent can be applied to an internal surface within a chamber and allowed to dry. A reagent, such as, for example, an immobilized binding agent and/or a probe agent can be dried onto an independent support materials, which can then be placed into the reaction chamber. Alternatively, either the immobilized binding agent or the probe agent can be incorporated onto an independent support material and the other component can be supported on one of the internal wall within the reaction chamber. The internal walls of the reaction chamber can be porous, with the immobilized binding agent and/or the probe agent incorporated therein. This can be accomplished by, for example, using a macroporous membrane to form the internal wall(s) of the reaction chamber and compressing the membrane around the reaction chamber to prevent leakage of sample out of the desired area. The immobilized binding agent and/or the probe agent can be supported on beads. Such beads can comprise a polymeric material, e.g., agarose, polystyrene, polymethacrylate, polymethylmethacrylate, optionally encasing a magnetic material (such as, for example, gamma $Fe_2O_3$ and $Fe_3O_4$). The bead material can be selected such that suitable support can be provided for the species to be attached. A magnet can be included in such a biosensor to hold the magnetic beads in the reaction chamber and to stop them from moving to the detection chamber. For example, the immobilized binding site can be positioned on magnetic beads within the reaction chamber.

Method of Use

Merely for the purpose of convenience, methods of using a biosensor described herein are described in terms of the embodiments illustrated in FIGS. 4-7. It is understood it is for illustration purpose only, and is not intended to limit the scope of the disclosure.

In use, a user can first introduce a fluid sample into the fill chamber and/or the reaction chamber. The sample can be drawn into the fill chamber and/or the reaction chamber under the influence of capillary or wicking action. The sample can be drawn into the fill chamber and/or the reaction chamber by an external force generated by a device such as, for example, a syringe, and/or a pump, and/or the user. The reaction chamber can comprise a vent that is open to the atmosphere, thus allowing air displaced by the sample to escape. Or the filling of the fill chamber and/or the reaction chamber by a fluid sample can displace air to the detection chamber. The volume of reaction chamber 122 can be chosen so as to be at least equal to and preferably larger than the volume of the detection chamber 128.

Entry of a biological sample, such as whole blood containing a target analyte, for example, an antigen, into the reaction chamber, can disperse magnetic beads from one internal surface and probe agent molecules from the other internal surface. The magnetic beads can be coated with the binding agent molecules. The binding agent can comprise an antigen. The probe agent can comprise a binding partner and a vehicle. The binding partner can be an antibody which can bind to the target antigen in the blood, and can bind to the immobilized binding agent, but with lower binding affinity. The vehicle can comprise, for example, PQQ encapsulated within a liposome, or PQQ surface bound to a polymer, such as a dendrimer. Each liposome can encapsulate multiple copies of PQQ. The presence of the target analyte in the sample can interfere the binding of the probe agent molecules to the binding agent molecules coated on a magnetic bead in a dose dependant manner.

After a given time, for example, about two minutes, a venthole can be punched, which can allow the transfer of reacted fluid sample by capillary action to the detection chamber. The detection chamber can comprise the reagents for the electrochemical measurement of the enzyme activity. The detection chamber can be sufficiently filled, namely, that sufficient sample is transferred to the detection chamber such that the presence of probe agent can be detected and analyzed by the detection method employed.

Magnets below the reaction chamber can prevent the transfer of magnetic beads and the probe agent molecules bound to the beads through the binding agent molecules. As a result, in this exemplary embodiment, the more target analyte in the fluid sample, the fewer probe agent molecules can bind to the immobilized binding agent molecules, and the more probe agent molecules can move to the detection chamber to be detected in the detection chamber.

The detection chamber can comprise apo-GDH and a liberating agent which can release the PQQ from the vehicle, and allow the interaction with the apo-GDH. If one vehicle contains, for example, 100 or more PQQ molecules, and each of these can bind and activate one apo-GDH, then the inhibition of a single antibody-PQQ-liposome probe agent binding to the magnetic beads can lead to the activation of 100 or more GDH molecules. In this way, as little as 5 µM antigen, for example, can be detected, if for example each liposome contains 100 PQQ's, or 500 fM if each contains 1000 PQQ's.

The skilled artisan will recognize the applicability of various configurations and features from different embodiments described herein. Similarly, the various configurations and features discussed above, as well as other known equivalents for each configuration or feature, can be mixed and matched by one of ordinary skill in this art to perform methods in accordance with principles described herein. It is to be understood that examples described are for illustration purposes only, and are not limiting as to the scope of the invention.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

The invention claimed is:

1. A device for detecting a target analyte in a fluid sample, the device comprising:
 a reaction chamber, wherein the reaction chamber comprises internal surfaces, a binding agent and a probe agent, the probe agent comprising a binding partner and a vehicle, wherein the binding partner is bound to the vehicle, wherein the target analyte in the fluid sample can react with the binding agent or the binding partner, wherein the vehicle comprises a plurality of copies of an activating agent;

a detection chamber, wherein the detection chamber comprises a detecting agent, wherein the activating agent can activate the detecting agent; and a fluid passageway between the reaction chamber and the detection chamber, wherein the device is adapted to move the reacted fluid sample from the reaction chamber to the detection chamber through the fluid passageway via capillary action, and wherein the presence of the target analyte in the fluid sample at a concentration results in a change in the amount of probe agent that moves with the reacted fluid sample to the detection chamber, wherein the change is detectable in the detection chamber and dependent on at least a threshold of the concentration.

2. The device of claim 1, wherein the binding agent and the probe agent are bound to different internal surfaces of the reaction chamber.

3. The device of claim 1, wherein the binding agent comprises at least one magnetic bead.

4. The device of claim 1, wherein the vehicle comprises from about 10 to about 100000 copies of the activating agent.

5. The device of claim 1, wherein the activating agent is encapsulated within the vehicle, wherein the vehicle comprises at least one lipidic particle.

6. The device of claim 1, wherein the activating agent is bound to the vehicle, wherein the vehicle comprises at least one polymer.

7. The device of claim 1, wherein an unactivated agent is immobilized in the reaction chamber, wherein the unactivated agent can bind to an unbound or unencapsulated activating agent.

8. The device of claim 7, wherein the unactivated agent comprises at least one magnetic bead.

9. The device of claim 1, wherein the detection chamber comprises a liberating agent, wherein the liberating agent can liberate the activating agent from the vehicle.

10. The device of claim 9, wherein the liberating agent comprises at least one agent selected from a mild detergent, a lytic peptide, an enzyme, heating, cooling, ultrasonication and a light source together with a photochemically activated lysing agent which is incorporated into the vehicle.

11. The device of claim 1, wherein the activating agent comprises a cofactor for an apoenzyme, wherein the detecting agent comprises the apoenzyme which can be activated by the cofactor.

12. The device of claim 11, wherein the cofactor comprises flavin adenine dinucleotide, wherein the apoenzyme comprises apo-glucose oxidase.

13. The device of claim 11, wherein the apoenzyme comprises a glucose dehydrogenase.

14. The device of claim 13, wherein the cofactor comprises pyrolloquinoline quinone, wherein the apoenzyme comprises apo-glucose dehydrogenase.

15. The device of claim 13, wherein the cofactor comprises flavin adenine dinucleotide.

16. The device of claim 11, wherein the detection chamber further comprises at least one mediator, wherein the mediator comprises one substance selected from dichlorophenolindophenol, phenazine ethosulphate, ferricyanide, ferrocene and complexes between transition metals and nitrogen-containing heteroatomic species.

17. The device of claim 1, wherein there is an openable vent in the distal end of the detection chamber.

18. The device of claim 1, wherein the detection chamber comprises at least two electrodes for detecting an electrochemical reaction in the detection chamber.

19. The device of claim 18, wherein at least one of the electrodes is formed from an electrically conductive layer, and further wherein there is a break in the electrically conductive layer that serves to define at least one edge of the electrode in the detection chamber.

20. The device of claim 18, wherein at least one electrode comprises palladium, platinum, gold, iridium, carbon, carbon mixed with binder, indium oxide, tin oxide or a mixture thereof.

21. A method of detecting a target analyte in a fluid sample, comprising:

delivering the fluid sample to the device of claim 1;

allowing a reaction to proceed in the reaction chamber between the binding agent and the probe agent, wherein the presence of the target analyte in the fluid sample at a concentration results in changes in the amount of probe agent bound in the reaction chamber and in the amount of unbound probe agent, wherein the changes are dependent on the concentration of the target analyte;

moving the reacted sample fluid from the reaction chamber into the detection chamber by capillary action such that the unbound probe agent moves to the detection chamber; and detecting presence of the probe agent in the detection chamber via a detecting agent, wherein the presence of the probe agent in the detection chamber is a measure of the concentration of the target analyte in the fluid sample, wherein one copy of the activating agent can activate at least one copy of the detecting agent.

22. The method of claim 21, wherein the moving of the sample from the reaction chamber to the detection chamber comprising opening a vent.

23. The method of claim 21, further comprising quantifying electrical signals received from the detection chamber, wherein the magnitude of the electrical signals is dependent on the concentration of the target analyte in the sample fluid.

* * * * *